United States Patent [19]

Dioguardi et al.

[11] Patent Number: 4,473,081

[45] Date of Patent: Sep. 25, 1984

[54] MULTICHANNEL PROGRAMMABLE BAND COMPARATOR FOR APPARATUS USED IN CARDIAC SURGERY

[75] Inventors: Nicola Dioguardi; Elena Allorio; Mila Bertinetti, all of Rome, Italy

[73] Assignee: Consiglio Nazionale Delle Ricerche, Rome, Italy

[21] Appl. No.: 261,778

[22] Filed: May 8, 1981

[30] Foreign Application Priority Data

May 14, 1980 [IT] Italy ............................... 22034 A/80

[51] Int. Cl.³ ............................................. A61B 5/00
[52] U.S. Cl. .................................................. 128/670
[58] Field of Search ............... 128/670, 695, 696, 706, 128/709, 710

[56] References Cited

U.S. PATENT DOCUMENTS

| | | | |
|---|---|---|---|
| 3,513,833 | 5/1970 | Finch et al. .......................... | 128/709 |
| 3,552,386 | 1/1971 | Horth .................................. | 128/703 |
| 3,857,383 | 12/1974 | Sommerfeld et al. ............... | 128/906 |
| 3,948,250 | 4/1976 | Weisman ............................. | 128/706 |
| 4,083,366 | 4/1978 | Gombrich et al. .................. | 128/706 |
| 4,193,393 | 3/1980 | Schlager ............................. | 128/702 |

Primary Examiner—William E. Kamm
Attorney, Agent, or Firm—Bucknam and Archer

[57] ABSTRACT

A multichannel programmable band comparator is provided for apparatus used in cardiac surgery. A plurality of transducers supply signals relating to parameters such as the blood flow, arterial and venal pressure, body temperature and acid-base equilibrium to a multiplexer. The multiplexer supplies an analog-to-digital converter which is connected to a comparator. The comparator receives upper and lower limit values which are preset in a memory and operates a visual and acoustic alarm via a demultiplexer if any parameter is outside the band defined by the corresponding upper and lower limit values. The multichannel comparator may be used during open heart surgery, when the cardiocirculatory and respiratory functions of a patient are taken over by complex apparatus, to ensure that various physiological parameters remain within acceptable limits.

5 Claims, 36 Drawing Figures

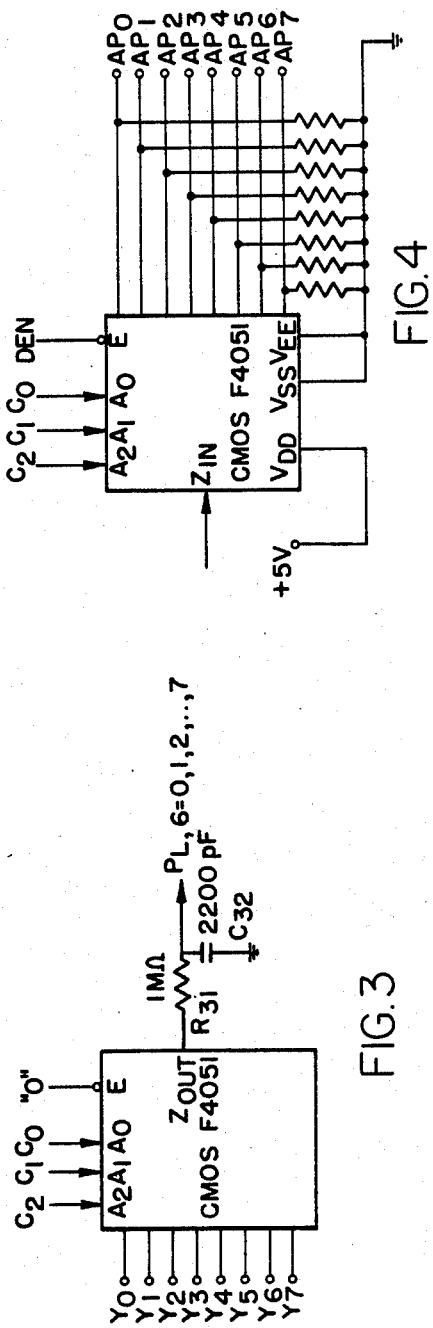
FIG.4
FIG.3
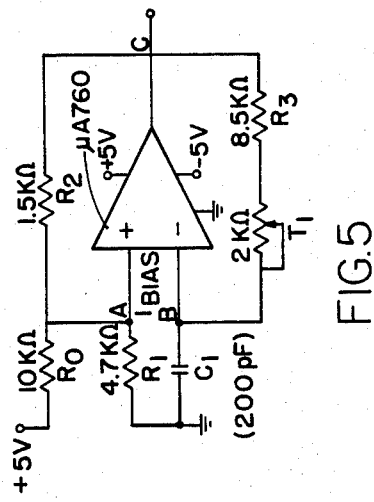
FIG.5

MULTICHANNEL PROGRAMMABLE BAND COMPARATOR FOR APPARATUS USED IN CARDIAC SURGERY

BACKGROUND OF THE INVENTION

1. Field of the Invention

The invention relates to multichannel programmable band comparators for apparatus used in cardiac surgery. During open heart surgery it is necessary to substitute for the cardiocirculatory and respiratory functions of the patient for a certain period of time using artificial apparatus. If such complex cardiac surgery, on which the life of a patient depends, is to have a successful outcome, the complex "machine" which is to substitute for the heart and lungs must operate correctly by reproducing conditions which are as similar as possible to actual physiological conditions. It is therefore equally vital to maintain under constant control delicate parameters such as blood flow, arterial and venal pressure, body temperature and acid-base equilibrium.

2. Description of the Prior Art

These functions have up to now been directly controlled by the medical and paramedical staff responsible for this area by means of the observation of a certain number of instruments which check that the values of the various parameters in question do not diverge from optimum values.

Instruments designed to carry out this monitoring function are not at present available. Consequently there is a need for a single instrument which is able to ensure that a certain number of parameters (up to eight) remain within their assigned field of variation by warning the medical personnel, by means of acoustic or visual signals, if one or more functions is in an abnormal situation.

SUMMARY OF THE INVENTION

According to the invention there is provided a multichannel programmable band comparator for use in cardiac surgery, comprising a plurality of transducers adapted to provide signals indicative of physical parameters of a patient, a multiplexer arranged to multiplex the signals from said transducers and having an output, an analog-to-digital converter having an input connected to said output of said multiplexer, a memory adapted to store a plurality of upper and lower limits defining acceptable bands for said respective transducer signals, a comparator circuit arranged to compare signals from said analog-to-digital converter with said respective upper and lower limits obtained from said memory, and alarm means connected to said comparator circuit, whereby said comparator circuit actuates said alarm means to produce an alarm when any of said signals from said analog-to-digital converter is outside said respective acceptable band.

Such a comparator may typically process up to eight different signals. The instantaneous values of the individual quantities are read off from a digital display. A group of selectors is used to preset the physiological variation bands within which each parameters is to be maintained.

The apparatus compares the measurement carried out in the form of a signal with the limits of the corresponding band and indicates irregular behaviour by means of luminous warning lights and an acoustic alarm.

BRIEF DESCRIPTION OF THE DRAWINGS

The present invention will become more evident from the following detailed description, given by way of example, of a specific embodiment of the invention which should not, however, be considered limiting as various modifications and variants falling within the scope of the present invention may be made to the device, this description being given with reference to the attached drawings, in which:

FIG. 3 shows the connections of the multiplexer shown in FIG. 1;

FIG. 4 shows the connections of the demultiplexer of FIG. 1;

FIG. 5 shows the connections of the differential comparator constituting the clock signal generation oscillator shown in FIG. 1;

Specific reference is now made to the instrument embodied in accordance with the principles of the present invention.

DESCRIPTION OF THE PREFERRED EMBODIMENT

Block Diagram

Figure 1:
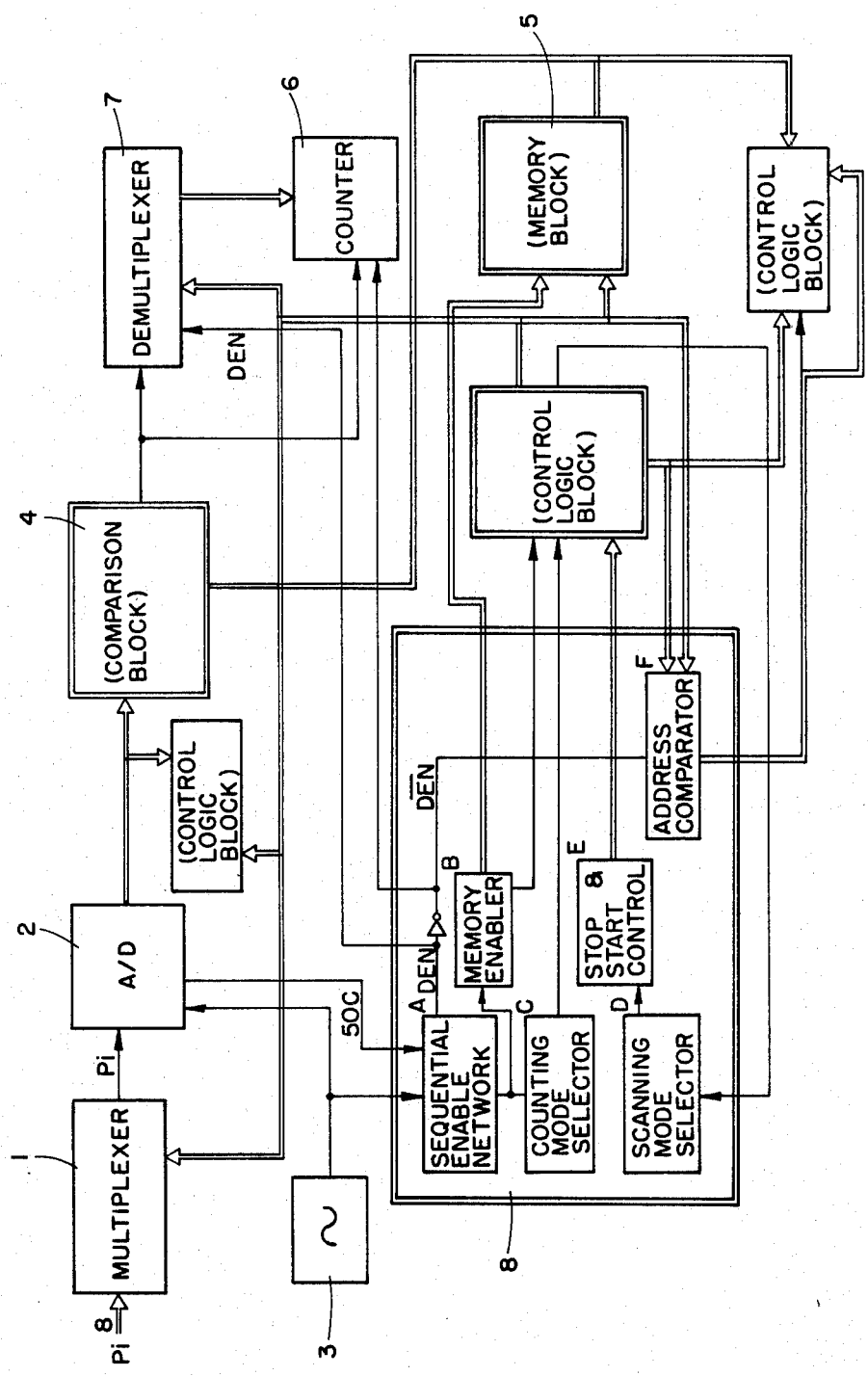
FIG. 1 shows a block diagram of the apparatus proposed by the invention.

The eight signals provided by the transducers are multiplexed in the multiplexer 1 shown in FIG. 1, with a frequency defined by the channel scanning counter.

The output signals from block 1 are then sent in succession to the analogue-digital (A/D) conversion block 2 which requires, for operation, an external clock timing signal generated by the oscillator 3.

The output of the A/D converter, composed of three and one half digits and coded in BCD (Binary-Coded-Decimal is sent to the comparison block 4 in addition to being displayed on a display. The converted signal is compared, separately, with the respective upper and lower limit values provided by the memory block 5.

The comparison operation provides a possible error signal which is used to light a luminous warning lamp and to actuate an acoustic warning. As shown with respect to block 6, a first counter, described in detail below, supplies the address of the channel examined both to the multiplexer 1 and to the memory block 5 thereby ensuring correspondence between the converted signal and the reference values with which it is compared, and then to a demultiplexer 7 which sends the error signal to the warning lamp corresponding to the channel in question.

A suitable end of conversion signal EOC is taken from the conversion block 2, which signal is processed together with the clock signal, in the control logic block 8. In this block important timing signals are generated, inter alia, those signals (DEN) for enabling operation of the demultiplexer 7 enabling access to the memories and those signals for stepping up the two counters.

The address of the first counter is sampled in order to be displayed so as to indicate the channel number at each instant, in addition to the uses described above.

The second counter controls the display of the variation limits and the channel to which reference is being made, with a frequency of one thirty-second of that of the first counter, so as to enable suitable permanence of the reference values on the relative display.

These values, supplied by the memory blocks 5, are pre-set when the instrument is actuated, by means of suitable BCD coded selectors contained in the data pre-setting block which will be described in detail

Operation of the individual blocks

Introduction

The operation of the individual blocks is described in the following paragraphs. This description is made without giving details relating strictly to circuit arrangements, except in the case of those components which have specific interest from the point of view of external connections required for design or in which the components are themselves particularly complex. For further circuit details reference should be made to FIGS. 39a-39d of the attached electrical diagram. The circuit was constructed using, for the most part, MOS (Metal Oxide Semiconductor) components.

With respect to the type of convention used throughout the design, the selection of the positive logic which associates the level "1" or "true" with the high voltage level is considered to be implicit.

Multiplexing and Demultiplexing

The eight analogue signals Pi supplied from the transducers should reach the conversion block 2 (FIG. 1) in an ordered sequence. The voltage levels of these signals vary between +2 V and −2 V.

For this initial operation a CMOS F4051 (FAIRCHILD) component was used. This integrated component which may be used both as a multiplexer and a demultiplexer, has eight analogue or digital independent inputs (outputs), $Y_0$-$Y_7$, one output (input) Z, three address inputs $A_2 A_1 A_0$ and an enable input $\overline{E}$ operating the low logic level "0".

In this way, the multiplexer was connected to the input of the circuit, with $V_{DD}=+5$ V and $V_{EE}=-5$ V, as shown in FIG. 3. The enable signal $\overline{E}$ is connected directly to earth as there is never a requirement for channel scanning to be discontinued; in this situation the output Z is always connected to one of the eight inputs. The output signal is however connected in series with a resistor $R_{31}$ to the conversion block for subsequent processing; this resistor $R_{31}$ which together with a capacitor $C_{32}$ connects the output to earth, acts as an input protection for the A/D converter 2 and in addition prevents transition oscillations due to the opening and closing of the switches.

The same component F4051 was used for the final demultiplexing operation of the error signal (ERROR). The outputs, connected to earth by means of a resistor of 6 kohm, are supplied to the luminous warning light for a parameter whose value does not lie within the related variation range. The ERROR input and the outputs $AP_0$-$AP_7$ are, in this example, logic signals, and therefore $V_{EE}$ is connected to $V_{SS}=0$ V. The enable signal DEN supplied by the control logic block 8 (FIG. 1) has a wave-form such as to enable the passage of the ERROR information to the respective luminous warning light only in a temporal gate during which the ERROR code is certainly correct as will be explained below.

The type of connections used are shown in FIG. 4.

Generation of the clock signal

The clock signal of the circuit is generated by the oscillator 3 of FIG. 1, constituted by a differential comparator μA760 (FAIRCHILD) suitably connected to operate as a square wave generator and to oscillate at the desired frequency. The type of connections used is shown in FIG. 5.

The clock signal is used in the A/D converter 2 of FIG. 1 and in the control logic block 8 of FIG. 1.

The selection of the clock frequency, $f_{clock}$, was carried out on the basis of considerations aimed at optimising the operation of the converter. For details of these considerations reference should be made to the paragraph relating to conversion.

The design oscillation has a frequency $f_{clock}$ of 102.400 kHz.

The differential comparator 3 requires two supplies V+ and V− which are typically of ±4.5 V to ±6.5 V and, in any case, are not higher than ±8 V.

In the example in question the following value was selected: V+ = +5 V and V− = −5 V.

The voltage $V_B$ at the terminals of the capacitor $C_1$ is applied to the inverting input (−) and therefore constitutes the input signal of the comparator μA760. Each of the two reference voltage levels $V_A$ (non-inverting input) assumes a value which depends on the output condition. The transient of the voltage $V_B$ is such as to bring it to the level of $V_A$; at this moment the comparator μA760 commutes and the logic level of the output voltage $V_C$ is inverted.

Figure 6:
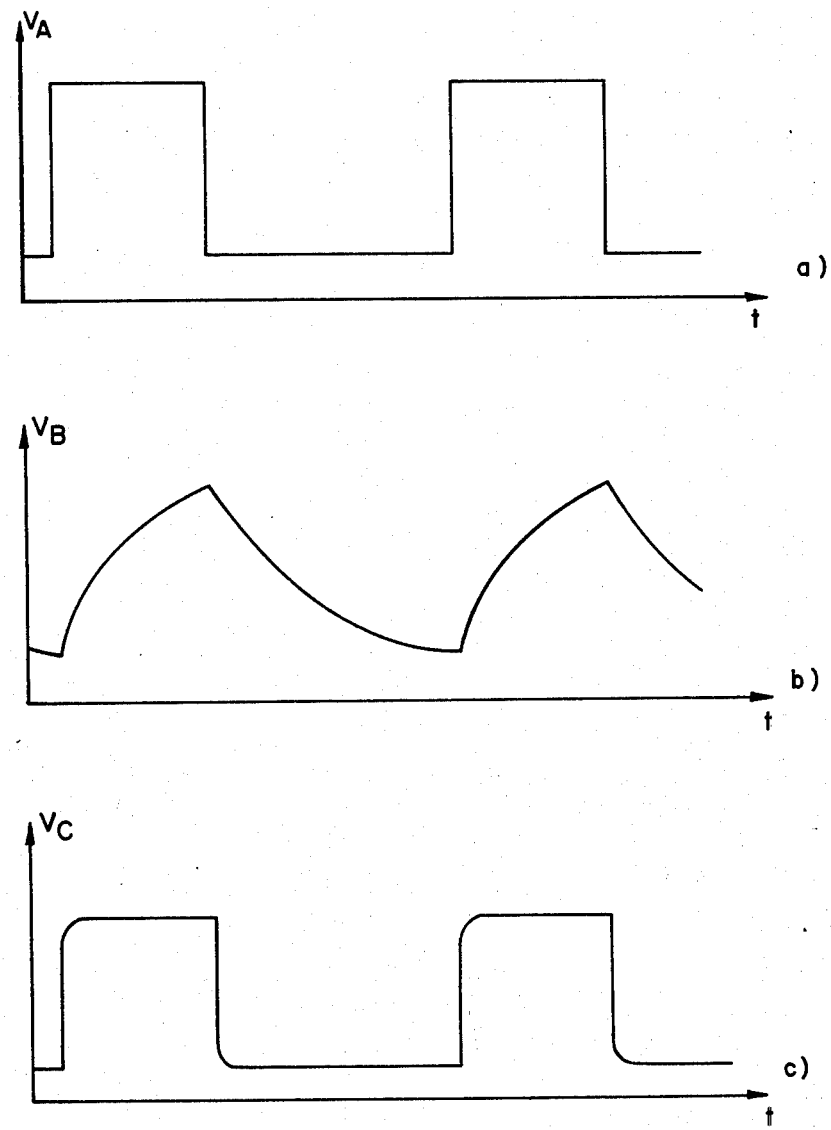
FIG. 6 shows the development in time of the input and output voltages of the differential comparator of FIG. 5.

The qualitative shapes of the three voltages are shown in FIG. 6.

The values selected for the resistors $R_0$–$R_3$ and for the trimmer $T_1$ and the capacitor $C_1$ enable, by means of the adjustment of the trimmer $R_5$, the calibration of the oscillator at the required frequency $f_{clock}$ = 102.4 kHz.

With further reference to FIG. 6c, the discharge time of the capacitor $C_{51}$ is greater than its loading time, thereby unbalancing the dwell times of $V_C$ at the logic condition "1" or "0"; this unbalancing does not however exceed the maximum unbalance tolerated by the A/D converter and therefore one of the two conditions continues for 70% of the time.

Analogue-digital conversion and display of the measurement

The pressure signal selected by the multiplexer is converted from analogue to digital in the conversion block.

Figure 7:
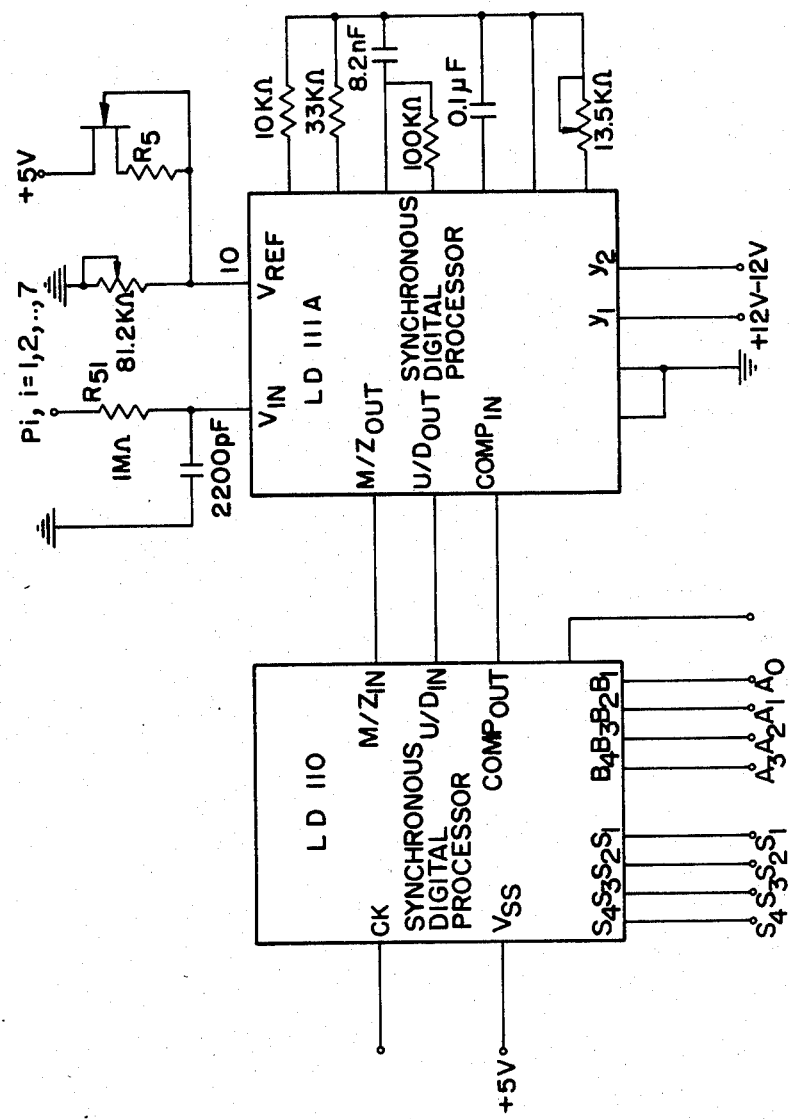
FIG. 7 is a diagram of the electrical connections of the analogue-digital converter of FIG. 1.

In accordance with the invention, a new type of converter made by Siliconix, composed of two integrated components LD110 and LD111A suitably connected together was used, as shown in FIG. 7.

The synchronous digital processor PMOS LD110 provides for the counting, maintenance and multiplexing of the data and for the control of the quantified load balancing function carried out by the analogue processor. It contains in addition seventeen static latches (bistable) in order to preserve the three and a half digits coded in BCD, the OVERRANGE and UNDERRANGE signals and the polarity of the input signal SIGN A. Nine output buffers supply the sign, the data coded in BCD ($A_3$, $A_2$, $A_1$, $A_0$) which has been multiplexed and the strobes (S4, S3, S2, S1) relating to the digits which are made available in sequence at the output. All these signals are operative in the logic condition "1".

The external clock signal which is generated by the differential comparator μA760 (FIG. 5), is used within the integrated digital component.

The external clock signal must oscillate at one of the 51 frequencies suggested by Data Sheet which may be determined from the equation $$f_{clock} = (2048)/(n)f_{network},$$

in which n = 1, 2, ..., 51

In order to obtain the maximum conversion speed, n = 1 was selected so as to obtain, for $f_{network}$ = 50 Hz, a clock signal which oscillates at 102.4 kHz. The converter therefore carries out a conversion every 60 msec. Each of the eight pressures is sampled and converted every 480 msec.

The A/D converter was connected externally as shown in FIG. 7. The reference voltage $V_{ref}$ of 2 V which it is necessary to supply to the Pin 10 of the integrated component LD111A was obtained by connecting a current limiter provided by a JFET transistor to a resistor which connects source and gate.

The drawback of the having the data in BCD available in sequential rather than parallel output was countered by storing the bits relating to the second and third digits D2: $A_{23} A_{22} A_{21} A_{20}$ and D3: $A_{33} A_{32} A_{31} A_{30}$ with two QUAD D-FLIP FLOP of TTL type (LS175) shown in FIG. 9, which acquire the data when they receive as clock signal the strobe (S2 or S3).

These flip-flops are "edge triggered", i.e. they may be commuted at the edge by a pulse.

The fourth digit D4 is constituted by single bit $A_{40}$ = AMAX, and is stored by a D FLIP FLOP F4013 CMOS.

Figure 8:
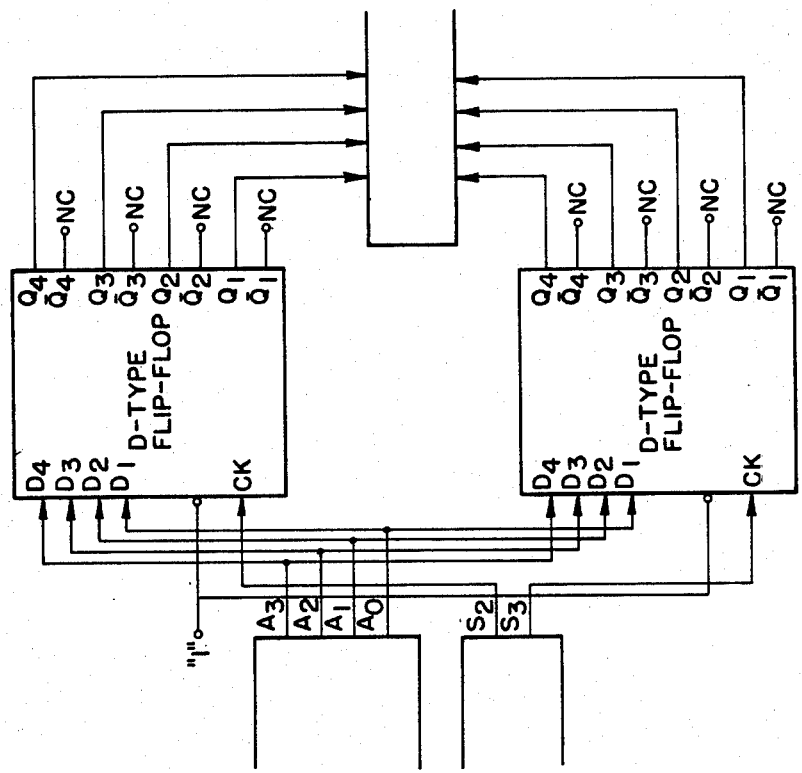
FIG. 8 is a logic diagram of the D-type flip-flops and their connections.

Only the second D2, third D3 and fourth digits D4, which are used in the comparison block 4 of FIG. 1, are retained at these latches, and are therefore available in parallel (as in FIG. 8).

During the construction of these connections, an incorrect synchronization was detected between the appearance of the bits relating to a digit ($A_{i3} A_{i2} A_{i1} A_{i0}$, i = 1,2,3,4) at the outputs and the respective strobe signal.

Figure 9:
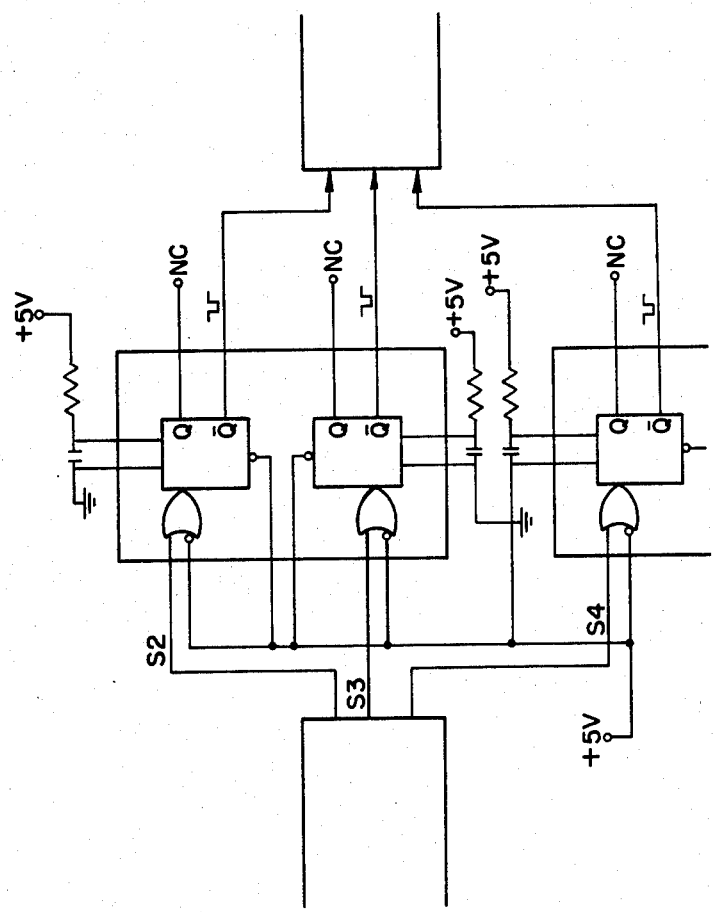
FIG. 9 is a logic diagram of the monostable delay circuits of FIG. 8.

In order to obtain correct data acquisition, it became necessary to delay by at least 35 μs the strobe signals using monostables MC14528 (MOTOROLA) connected externally with adequate resistance and capacitance values, as shown in FIG. 9.

Figure 10:
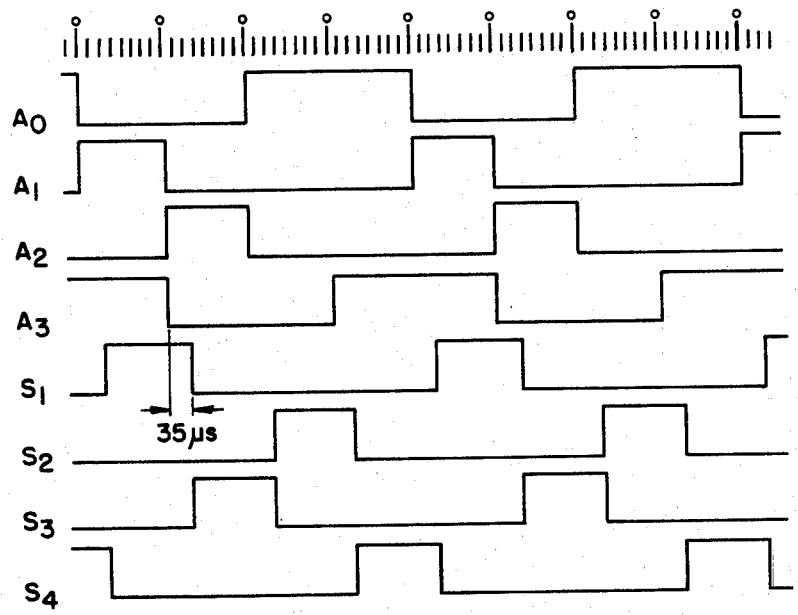
FIG. 10 is a specific example of correct synchronization of the strobes with the data.

In this way the leading edge of the strobes appears with certainty within the period corresponding to eight clock pulses (78.125 μs) during which the converter presents the respective bits. An example of correct synchronization is shown in FIG. 10.

In order to display the result of the conversion, the four signals $A_3 A_2 A_1 A_0$ which represent the three less significant digits in the sequence D1 D3 D2 and D4 regulated by the strobes, are connected to three "BCD-To-Seven-Segments" drivers, in this case F4511, which serve to drive the display shown on the control panel.

Figure 11:
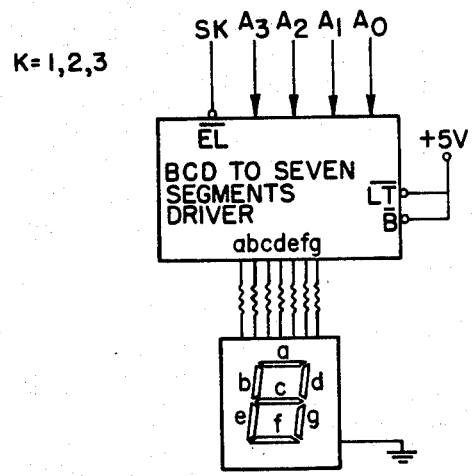
FIG. 11 shows the display of three less significant digits with the drives and the display device.

These integrated components require a signal $\overline{EL}$ which is operative at the level "0" in order to accept the input data. In accordance with the invention, these enabling signals are constituted by the first three strobes S1, S2 and S3, suitably inverted. This operation is shown in FIG. 11.

Figure 12:
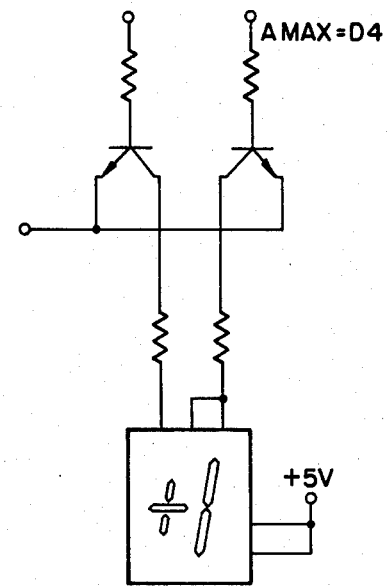
FIG. 12 shows the display system for the fourth digit.

The display which shows the fourth digit D4 = AMAX, stored in a latch, and the polarity of the converted signal SIGN A is however driven by way of two transistors connected so as to function in the saturation or cut-off zone and to enable the passage of the current required to light up the luminous segments of the display, as shown in FIG. 12.

For this purpose, the LITRONIX component DL-701 having a common anode was used, whilst for the remaining digits use was made of the component D1-702 having a common cathode.

In order to obtain a reading of the values, directly in pressure units and remembering that a millimeter of $H_2O$ or a millimeter of Hg corresponds to 10 mV in accordance with the measurement units used, the first digit D1, which represents the millivolts of the voltage measured, is separated by a point from the more significant digits.

With reference to the A/D converter 2, it has been seen that in normal conditions the analogue input of LD111A (FIG. 7) should not be exposed to voltages greater than $+12$ V (or lower than $-12$ V). In order to prevent a situation of this type, a resistor $R_{51}$ is connected in series with the input Pin in order to limit the input current which may be at the maximum 1 mA. The value selected of 1 mΩ ensures protection of the input up to a voltage of 1000 V.

The size of the error introduced by the resistor considering the high impedance of the input which is approximately $10^{12}$ ohm, does not affect the input signal since it is at maximum approximately $10^{-6}$, which is negligible given the resolution of $10^{-3}$ of the apparatus.

In the case in which the input (Pi, i=0, 1, . . . , 7) exceeds the permissible range of $\pm 2$ V, the disappearance of transitions on the strobe lines enables the coding of an overflow signal OW, which is then displayed on the control panel by a luminous diode, using a NOR-gate which achieves the expression $$OW=(S1+S2+S3+S4)'.$$

In a similar way it is possible to obtain an end of conversion signal EOC, using the signals M/Z (Measure Zero Logic), U/D (Up/Down) and COMP (Comparator output) in accordance with the expression $$EOC=(M/Z+U/D+COMP)'.$$

In order to carry out this operation it is necessary to bring the COMP signal, which oscillates between $-12$ V and $+6$ V to the levels of the MOS logic at which the binary outputs U/D and M/Z are already located. This aim is achieved by connecting the output COMP to the inverting input of the voltage comparator µA311 (see FIG. 39), which carries out a comparison with the non-inverting input connected to earth.

Figure 13:
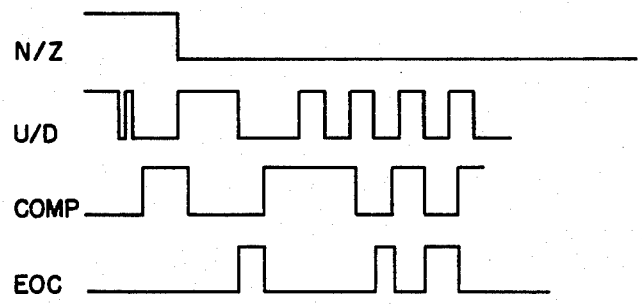
FIG. 13 is a diagram of the coding times for the end of conversion signal EOC.

Reference should be made to FIG. 13 for the time diagrams.

The end of conversion signal EOC is used in the control logic block in order to eliminate false signals due to the passage through the latches of data which refer to the intermediate approximations carried out by the converter.

The signal M/Z is used as an operating index of the converter, and drives a luminous warning light (CONVERSION IN PROGRESS) located on the control panel of the apparatus in order to indicate the correct alternation of the intervals of measurement and self zero-setting.

Comparison

The signals relating to each channel (supplied by the A/D conversion block 2 of FIG. 1), and containing the sign information (SIGN A="1" if positive, SIGN A ="0" if negative) and in BCD the two and a half more significant digits D4, D3, D2 (respectively $A_{40}$. $=$AMAX for the fourth digit, $A_{33}$ $A_{32}$ $A_{31}$ $A_{30}$ for the third and $A_{23}$ $A_{22}$ $A_{21}$ $A_{20}$ for the second) reach the comparison block 4. The coding of the UPPER and LOWER reference values (respectively U4: $B_{4OU}$, U3: $B_{33U}$ $B_{32U}$ $B_{31U}$ $B_{30U}$, U2: $B_{23U}$ $B_{22U}$ $B_{21U}$ $B_{20U}$ for the upper limit, L4: $B_{40L}$, L3: $B_{33L}$ $B_{32L}$ $B_{31L}$ $B_{30L}$, L2: $B_{25L}$ $B_{22L}$ $B_{21L}$ $B_{20L}$ for the lower limit) and the respective signs SU and SL reach the same block simultaneously.

The comparison block comprises two parts connected in cascade, and called block A and block B.

Block A—Comparators

Only the information relating to the second and third digits of the signal and the references enters block A.

The sub-blocks A1,A2,A3 and A4 are constructed physically of four four-bit binary comparators, in this case F40085, connected two by two in cascade.

Each of the two pairs supplies as output the result of the comparison carried out between the second and third digits of the pressure measurement and the UPPER (A1 and A2) and LOWER (A3 and A4) references.

Figure 14:
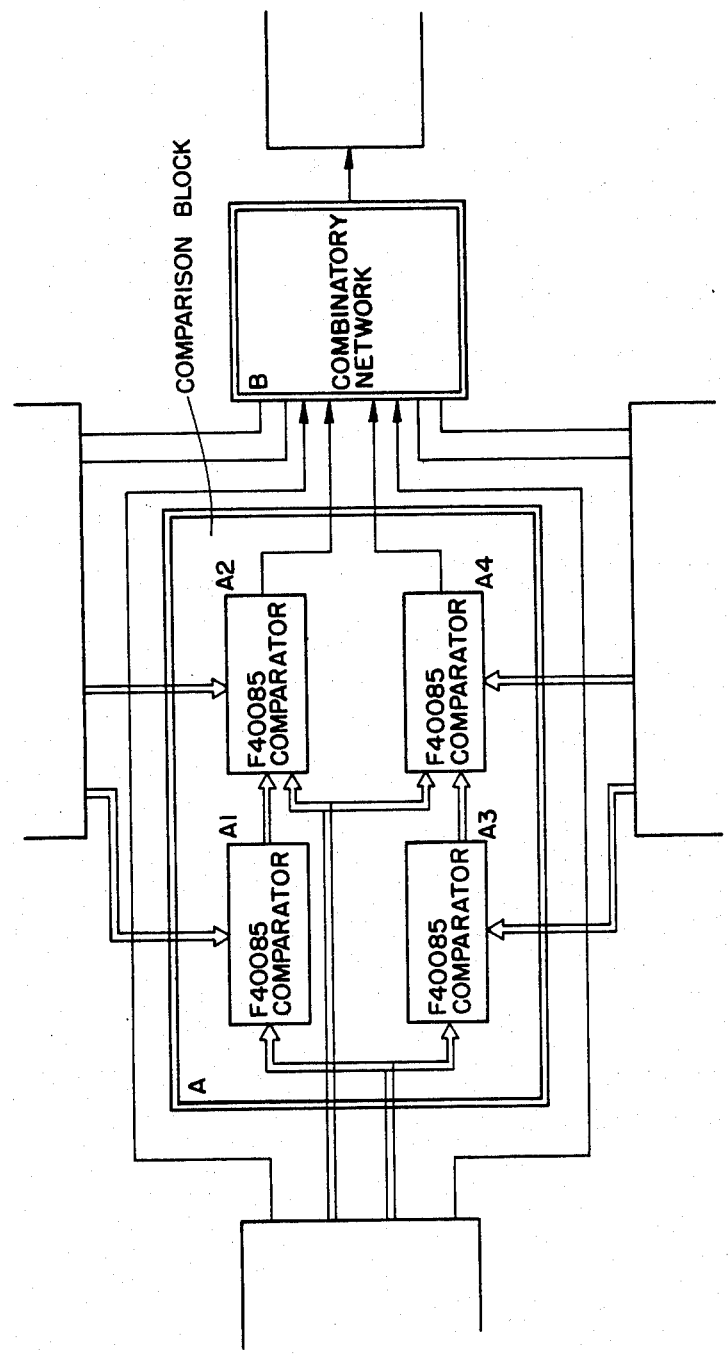
FIGS. 14 and 15 show how the cascade connection of comparators enables output information to be obtained with respect to the comparison undertaken.

By separate analysis of the behaviour of each comparison pair, FIG. 14 shows how the cascade connection of the two F40085 enables the information relating to the comparison to be obtained at the output.

Block B—Combinatory network for the comparison of the sign and the fourth digit It can be seen that eight bits of information are supplied to block B, i.e.

1 and 2: The signals D3D2 U3U2 and D3D2 L3L2 output from the blocks A2 and A4 which indicate the result of the comparison between the second and third digits of the measurement and the reference.

3: The most significant bit AMAX which constitutes the fourth digit of the measurement and the reference.

4: The sign, taken directly from the A/D converter 2 of FIG. 1.

5 and 6: The most significant bit U4 and the sign SU of the UPPER reference, supplied by the memory block 5 of FIG. 1.

7 and 8: The most significant bit L4 and the sign SL of the LOWER limit of each channel, these also being supplied by the memory block 5 of FIG. 1.

The synthesis of the combinatory network was carried out using the method of Karnaugh's maps individually for the coding of the error signal ERRORL relating to the comparison of the measurement with the LOWER limit, and for the coding of the error ERRORU obtained from the comparison of the measurement with the UPPER limit.

With respect to the coding of the ERRORL and ERRORU signals, these indicate that the pressure signal in question is outside of its variation range in the case in which one of the two is at the logic level "1".

In order to obtain the overall ERROR signal from the monitoring carried out, the outputs ERRORL and ERRORU are supplied to an OR-gate.

Figure 33A:
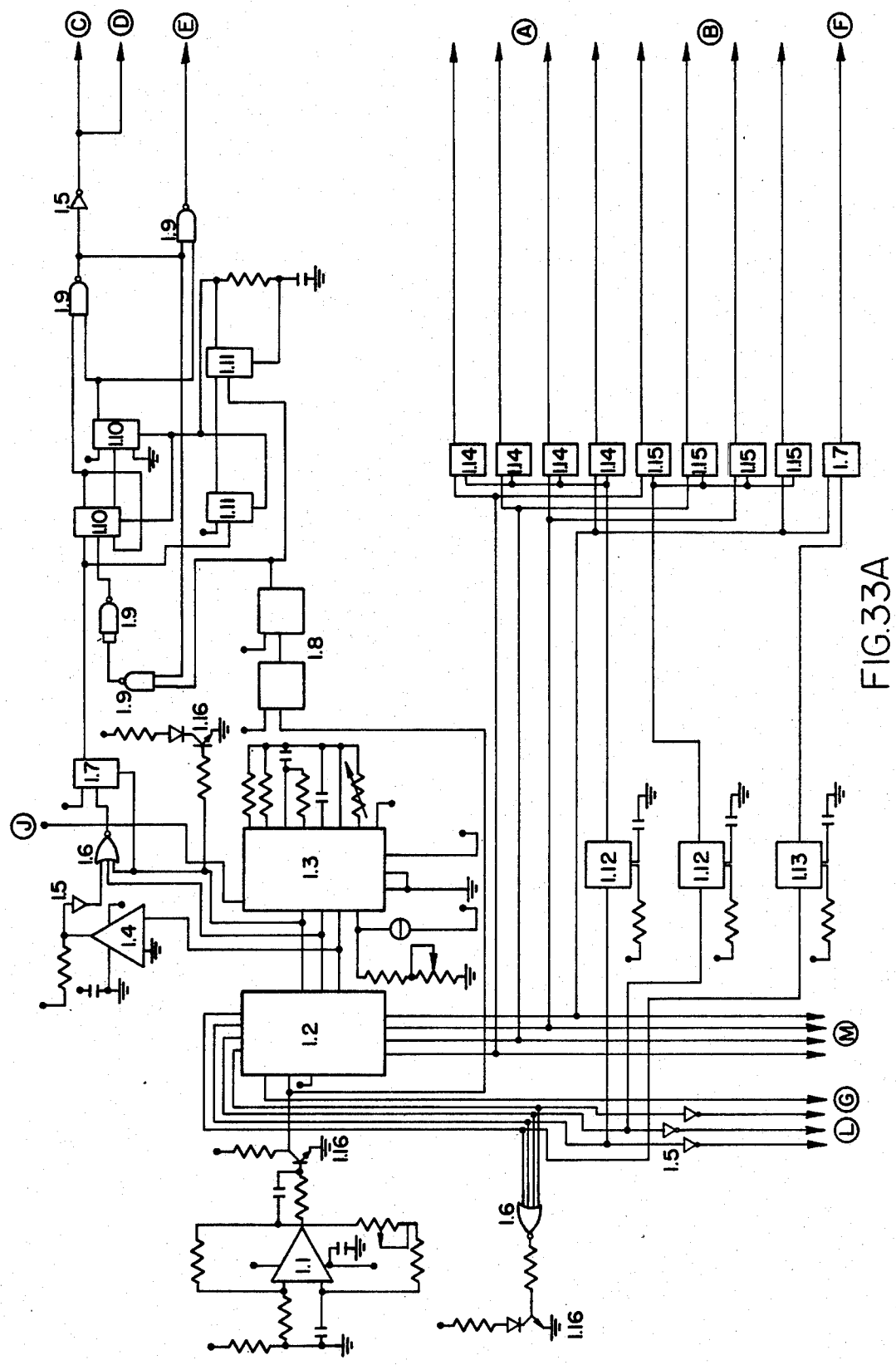
FIGS. 33A-33D are a diagram of the overall electrical operation of the apparatus of the invention.
Figure 33B:
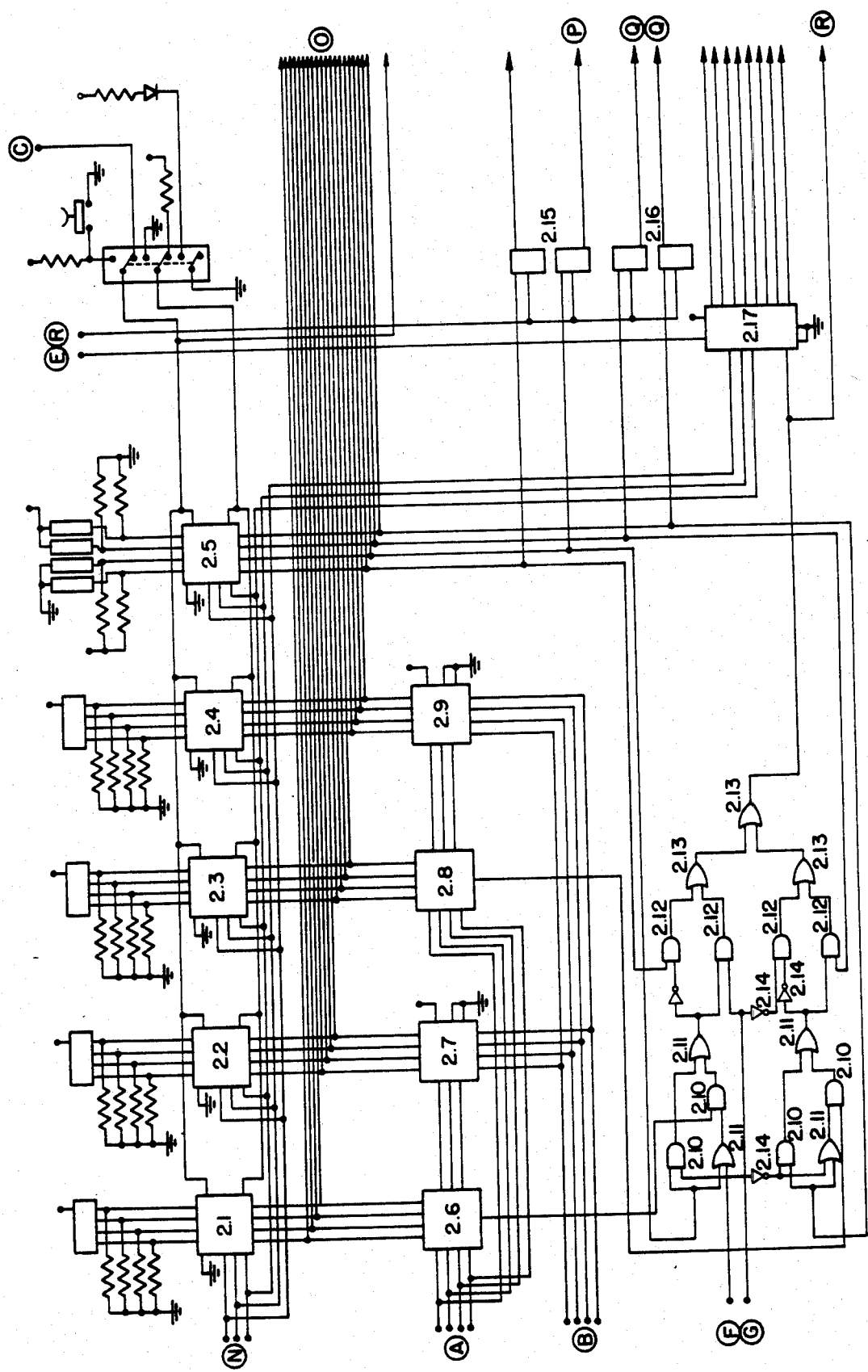
Figure 33C:
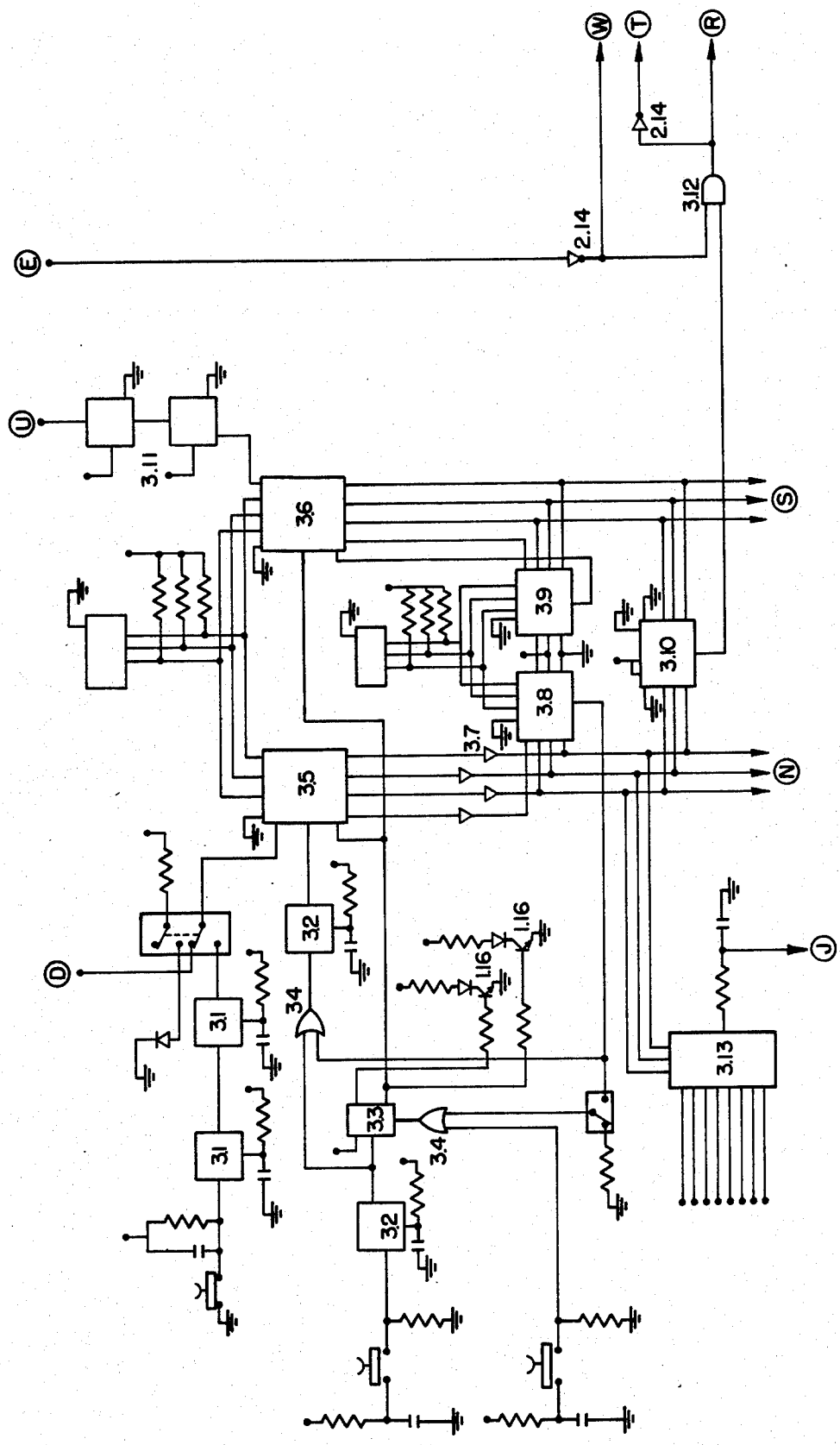
Figure 33D:
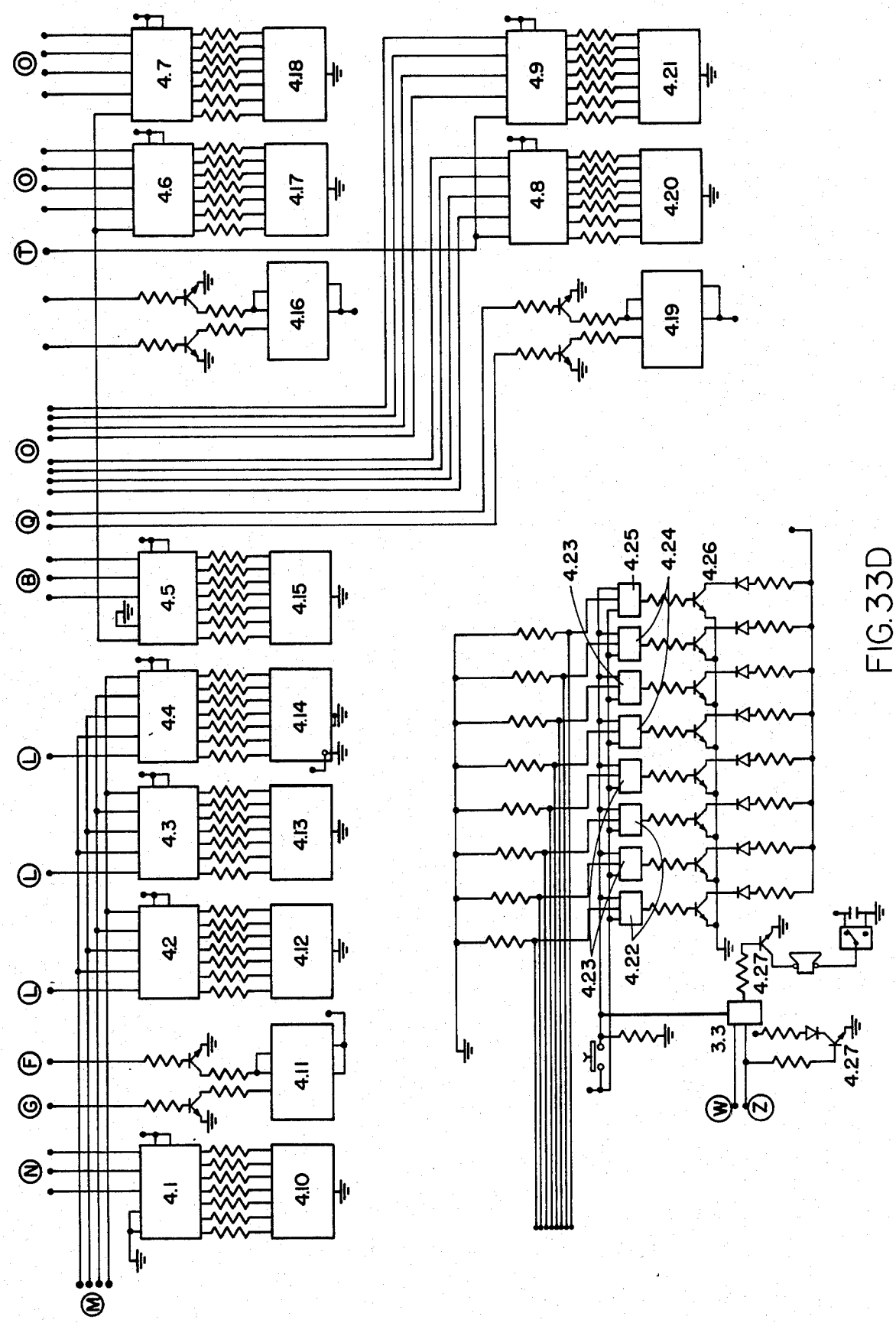

The overall combinatory network is shown in FIG. 33A.

In the case in which the parameter in question has exceeded the interval $\overline{L \: U}$ (ERROR="1"), the output signal is used to light a luminous diode ERROR and to actuate an acoustic alarm simultaneously; this operation is described below.

It is possible for the ERROR signal to transmit false information; this is due to the fact that the parameter measurements coming from the latches D4, D3, D2 may be the result of an intermediate approximation of the A/D converter. In order to eliminate such errors, a suitable signal is processed in the control logic block 8 of FIG. 1 which enables the demultiplexer, and therefore the illumination of luminous warning lamps relating to each channel, only when the compared data are correct data.

TABLE 1
TRUTH TABLE FOR THE CODING OF THE ERRORU SIGNAL

| SIGNA | SU | ΔMAX | U4 | D3D2>U3U2 | ERRORU |
|---|---|---|---|---|---|
| 0 | 0 | 0 | 0 | 0 | 1 |
| 0 | 0 | 0 | 0 | 1 | 0 |
| 0 | 0 | 0 | 1 | x | 1 |
| 0 | 0 | 1 | 0 | x | 0 |
| 0 | 0 | 1 | 1 | 0 | 1 |
| 0 | 0 | 1 | 1 | 1 | 0 |
| 0 | 1 | x | x | x | 0 |
| 1 | 0 | x | x | x | 1 |
| 1 | 1 | 0 | 0 | 0 | 0 |
| 1 | 1 | 0 | 0 | 1 | 1 |
| 1 | 1 | 0 | 1 | x | 0 |
| 1 | 1 | 1 | 0 | x | 1 |
| 1 | 1 | 1 | 1 | 0 | 0 |
| 1 | 1 | 1 | 1 | 1 | 1 |

$$ERRORU = \overline{SIGNA} \, \overline{SU}[\overline{AMAX}(U4 + (\overline{D3D2 > U3U2})) + U4(\overline{D3D2 + U3U2})] +$$
$$SIGNA[\overline{SU} + AMAX \, \overline{U4} + (D3D2 > U3U2)(AMAX + U4)]$$

TABLE 2
TRUTH TABLE FOR THE CODING OF THE ERRORU SIGNAL

| SIGNA | SL | ΔMAX | L4 | D3D2<L3L2 | ERRORL |
|---|---|---|---|---|---|
| 0 | 0 | 0 | 0 | 0 | 1 |
| 0 | 0 | 0 | 0 | 1 | 0 |
| 0 | 0 | 0 | 1 | x | 0 |
| 0 | 0 | 1 | 0 | x | 1 |
| 0 | 0 | 1 | 1 | 0 | 1 |
| 0 | 0 | 1 | 1 | 1 | 0 |
| 0 | 1 | x | x | x | 1 |
| 1 | 0 | x | x | x | 0 |
| 1 | 1 | 0 | 0 | 0 | 0 |
| 1 | 1 | 0 | 0 | 1 | 1 |
| 1 | 1 | 0 | 1 | x | 1 |
| 1 | 1 | 1 | 0 | x | 0 |
| 1 | 1 | 1 | 1 | 0 | 0 |
| 1 | 1 | 1 | 1 | 1 | 1 |

$$ERRORL = \overline{SIGNA}\,(SL + \overline{L4})(\overline{D3D2 < L3L2}) +$$
$$AMAX[\overline{L4} + (\overline{D3D2 < L3L2})] +$$

TABLE 2-continued
TRUTH TABLE FOR THE CODING OF THE ERRORU SIGNAL $$SIGNA \, SL[\overline{AMAX}(D3D2 < L3L2) + \overline{AMAX}\,L4]$$

Acoustic-luminous signals

The final aim of the invention, in addition to the values of the parameters Pi (or the fluxes) under surveillance, is to warn the operator, by means of an acoustic alarm, of the abnormal and non-physiological behaviour of one or more of the parameters concerning extracorporeal perfusion. The correspondence of the sound alarm with the parameter which is referred to is indicated by a luminous warning light associated with each channel.

Figure 15:
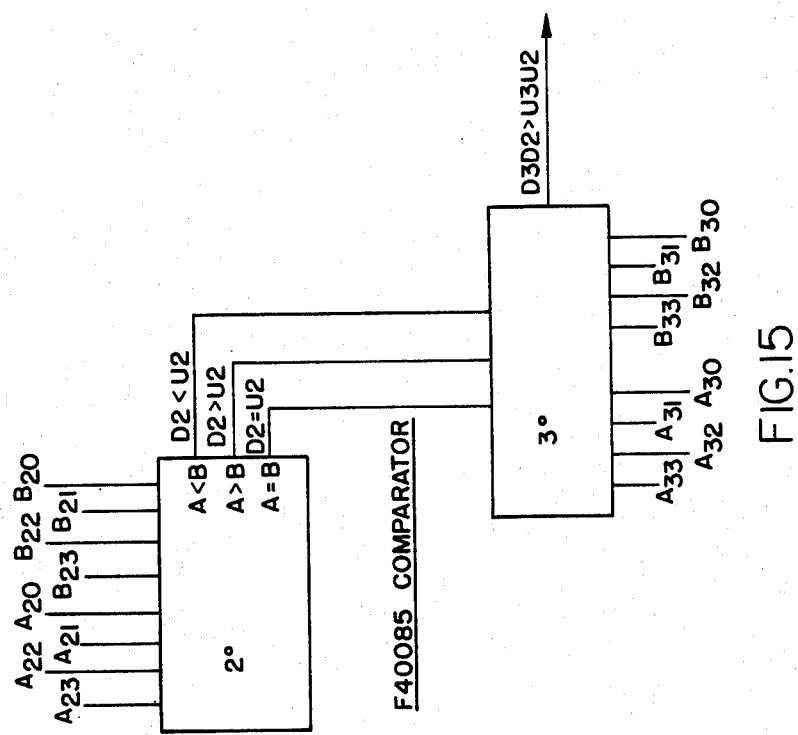

The block which comprises these functions is organized in accordance with the diagram of FIG. 15.

Figure 16:
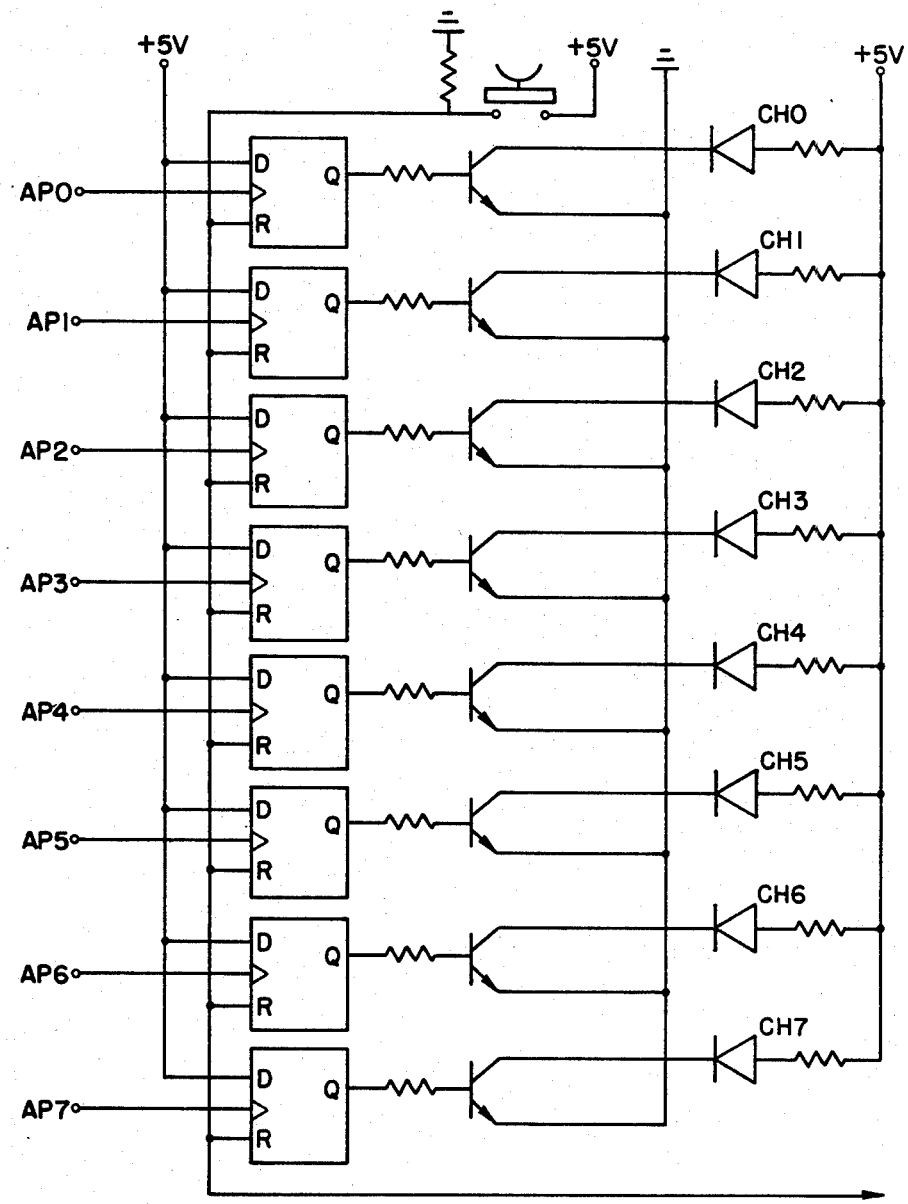
FIG. 16 shows in detail the acoustic/luminous signal unit of FIG. 1.

A level "1" of the signals APi output from the demultiplexer 7 represents the final coding of undesirable behaviour of the parameter monitored in the channel to which reference is made. Each of these signals is stored on a D-Flip Flop F4013 and controls, always in the case in which the level "1" is involved, the illumination of a warning light represented for example by a luminous diode. The connections which were carried out in this respect are shown in FIG. 16. The transistors are connected such as to function in a saturation or cut-off zone, in which case they enable the passage of the current required to illuminate the corresponding diode LED for the transmission of light. For these uses, matrices of seven transistors, NPN TRANSISTOR ARRAY CA 3081 (RCA) were used rather than discrete components.

The RESET signal, which zero-sets the outputs of the flip-flops is supplied by the external RESET pulser; without manual action on the pulser the diodes remain illuminated even if the parameter spontaneously returns within the variation limits which have been pre-set. This was designed to enable the experimenter to observe that the parameter had exceeded, even if only instantaneously, its fixed range which signifies, given the slow dynamics of the signals in question, the occurrence of a critical moment in the course of the parameter.

The ERROR information arriving from the comparison block 4 of FIG. 1 is also supplied to the D-flip flop ALA 191. However in this case it is supplied as data D, whilst the clock of the integrated component is constituted by the signal $\overline{DEN}$ generated in the control logic block 8 of FIG. 1.

This connection was used to prevent false ERROR codings from affecting the acoustic alarm.

Figure 17:
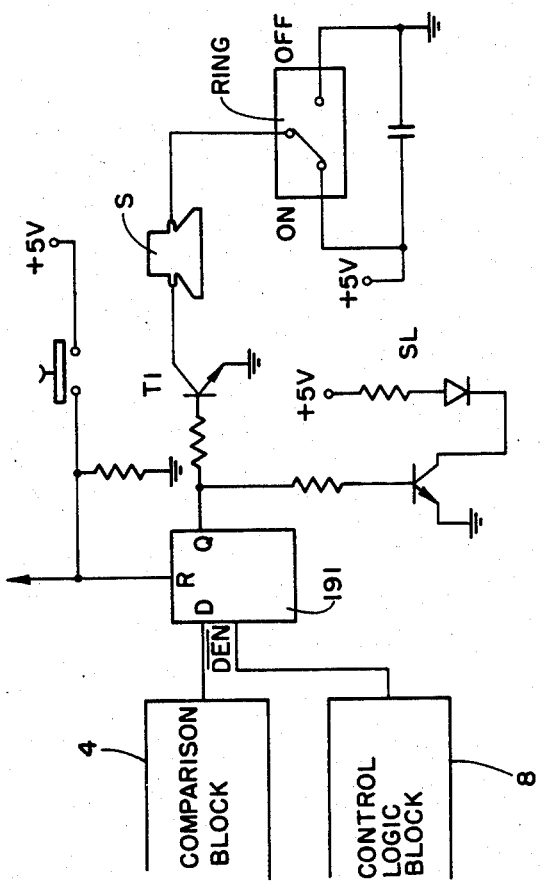
FIG. 17 shows in detail the control diagram for the acoustic and luminous signalling devices for the error signal.

The positive transition from "0" to "1" of $\overline{DEN}$ transmits the ERROR logic level, which is at this time certainly correct, to the output Q. The connections of these lines are shown in FIG. 17.

The transistor T1 which is polarized by the level of Q, enables the siren S when the transistor is operating in the saturation zone. The signal provided by means of the RESET pulser and already used to extinguish the warning lamps, i.e. the luminous error diodes, is also used to reset the flip-flop ALA 191 relating to the alarm bell system.

A switch RING (ON-OFF) enables the operation of the acoustic alarm to be discontinued. It should also be noted that the siren ceases spontaneously when the error state is corrected, whereas the visual alarms maintain the information until manually discontinued.

In the case in which the switch RING is in the OFF position, there is provided a luminous warning lamp ERROR (SL) which shows the condition of the flip-flop ALA 191. The optical information ERROR replaces the acoustic information and is designed to monitor continuously the actual state of normality or abnormality of the perameters in question. If, for example, a situation arises in which one or more alarm LED's are lit, but the error LED is off, this signifies that a condition has arisen in which one or more perameters have temporarily exceeded to predetermined limits, but have already returned within the required normal condition, i.e. within the said limits.

Control logic

The control logic block 8 of FIG. 1 is designed to carry out all those operations which serve to determine the counting and operational modes of the circuit and to generate the main timing signals which regulate the activity of the counters, the memories, the display mechanisms and the demultiplexer.

Many of the commands which determine the decisions taken within this block are provided externally by means of switches and pulsers. The specific functions of these decision-making instruments were designed in order to satisfy the widest range of requirements of the operator during operations involving extracorporeal perfusion.

Particular attention was paid to the consideration that, during an operation of this type, the need to carry out more exact monitoring of one of the parameters in question might possibly arise. This was taken into account either by providing for the setting of variation limits differing from those set initially (for example narrower limits) or by providing the possibility of pausing, at will, on the channel in question in order to enable continuous monitoring by means of the direct read-off of the measurements carried out by the instrument.

In order to simplify the description of the internal operation of the control logic block, the various operations which it carries out have been organised into sub-blocks.

Figure 18:
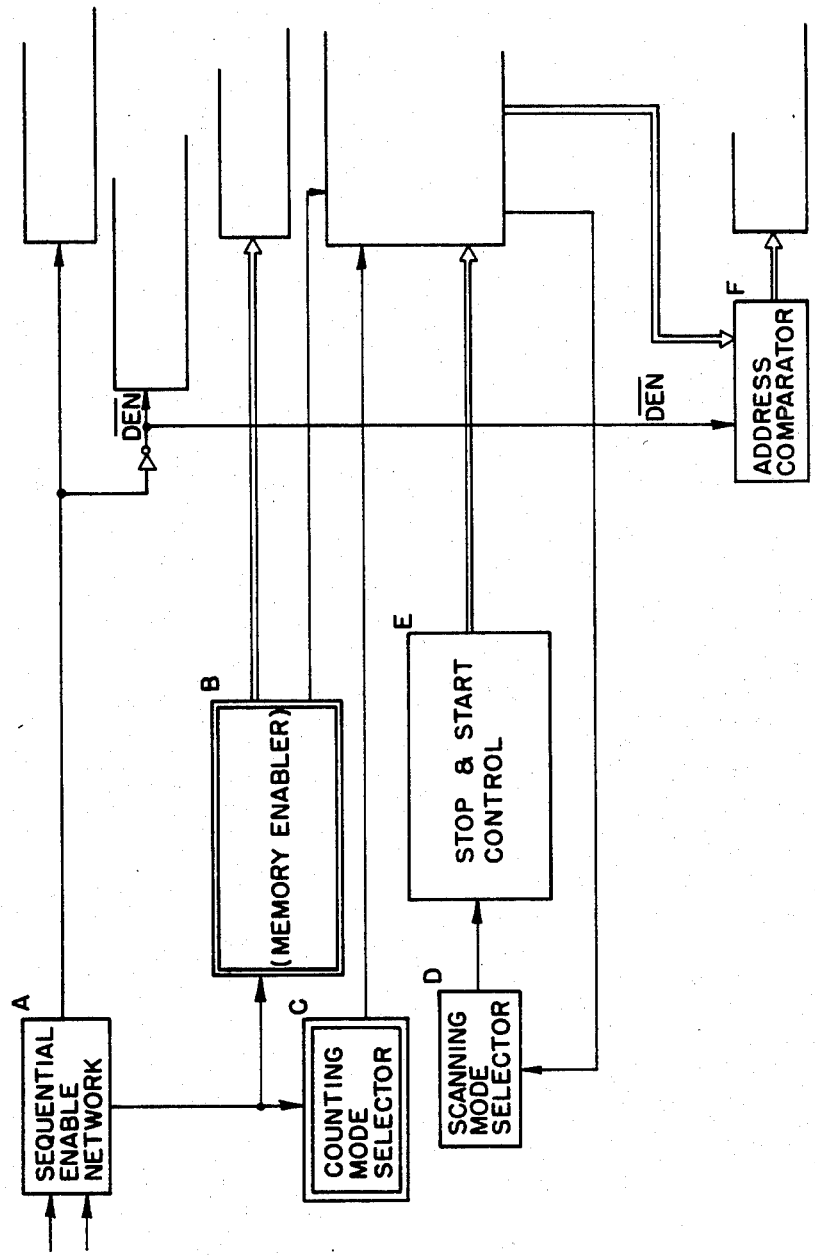
FIG. 18 shows the operational diagram of the control logic group.

An overall diagram is given in FIG. 18.

Block A—Sequential ENABLE network

It has already been shown that a false coding of the ERROR signal output by the comparison block 4 of FIG. 1 is possible as a result of the fact that the parameter signal D4 D3 D2 supplied by the latches may be the result of intermediate approximations carried out by the A/D converter. In order to prevent this false information from affecting the luminous and acoustic warnings provided by the apparatus, it is necessary to generate an enabling signal for the demultiplexer 7 which enables the information to pass to the acoustic-luminous signalling block only when it is certain that the comparison has been carried out with the exact data.

Figure 19:
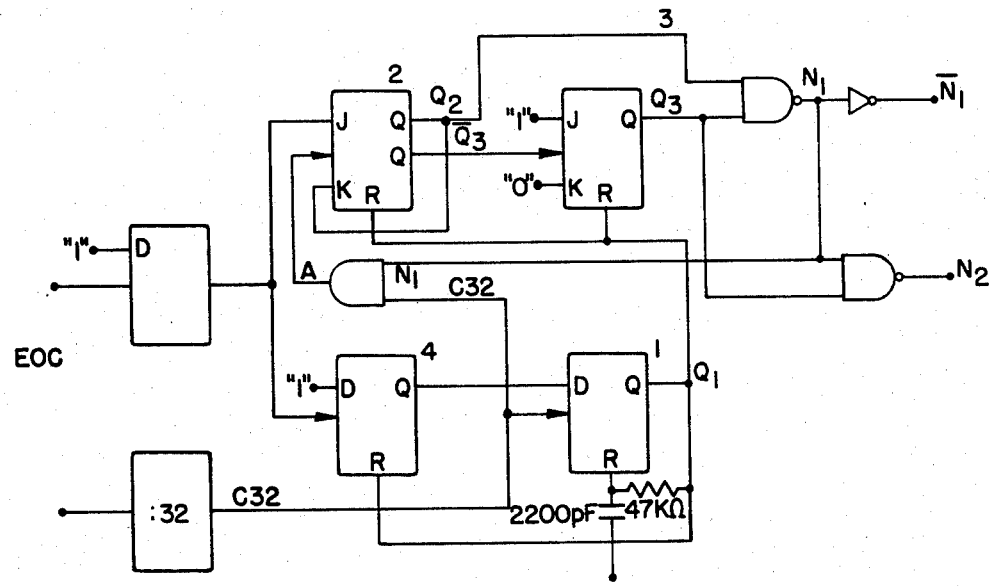
FIG. 19 shows the electrical diagram of the sequential ENABLE network.

. This object was achieved by means of a suitable sequencer, whose diagram is shown in FIG. 19.

The same network enabled the generation of a suitable signal $\overline{N}_1$ for enabling reading of the memories.

The signal EOC, coded in the conversion block (FIG. 13), has a shape of the type shown below:

Figure 20:
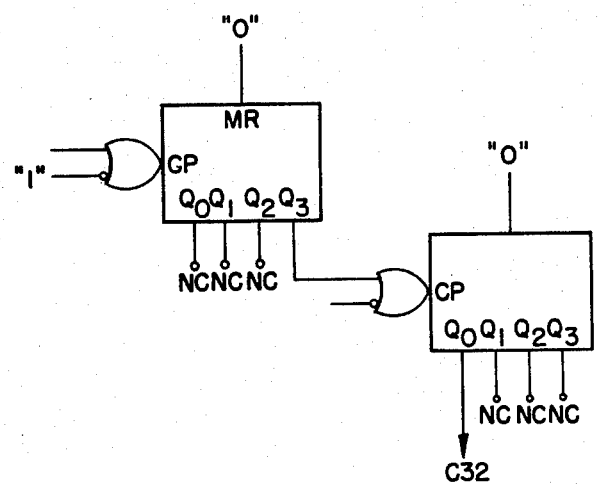
FIG. 20 shows the division of the clock signal obtained by means of a second binary counter.
Figure 21:
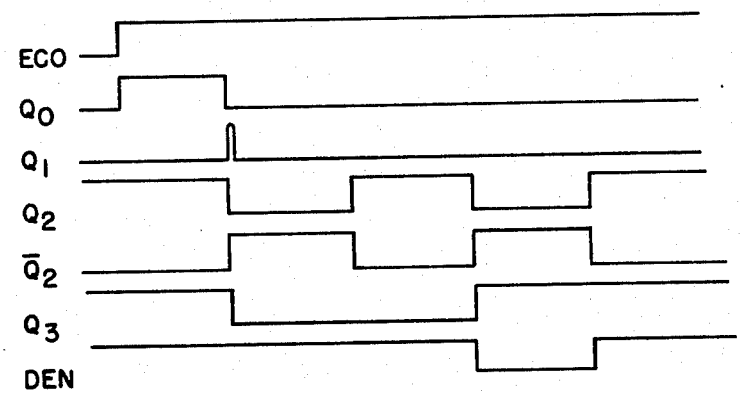
FIG. 21 shows the time diagram of the sequential ENABLE network shown in FIG. 19.

Given that the actual instant in which the conversion is finalized corresponds to the first transition "0" "1", the signal EOC acts as a clock for a flip-flop F4013 (as shown in FIG. 19) in order to ensure that the output maintains the information (of end of conversion) for the entire self zero-setting interval of the converter. The wave form obtained has the following shape:

The signal EOCF obtained in this way and the clock signal divided by 32 by means of a double binary counter F4250 connected as shown in FIG. 20, constitute the inputs of the sequential block A. The time diagrams of the signals provided in the network are shown in FIG. 21.

Block B—Enabling of the memory reading and writing operations

The memory block for the reference limits used for controlling the parameters is regulated, in respect of the two functions of reading and writing of the data, by two enabling commands WREN (write enable) and MEN (memory enable). The operation of writing of preset values on the external selectors, such as variation limits, only takes place when both the signals WREN and MEN are in the logic condition "0".

However, in order to carry out reading of the data which have been stored, and therefore to be able to proceed to the comparison operation the WREN enable must be at the logic level "1" whilst the condition "0" is still required for the MEN signal. Table 3 is a truth table and summarises the above:

TABLE 3

| MEN | WREN | OPERATIONS |
| --- | --- | --- |
| 0 | 0 | Writing |
| 0 | 1 | Reading |
| 1 | X | Information maintenance |

Table 3 also shows that a maintenance of the written data corresponds to a value "1" of MEN, irrespective of the state of WREN.

Figure 22:
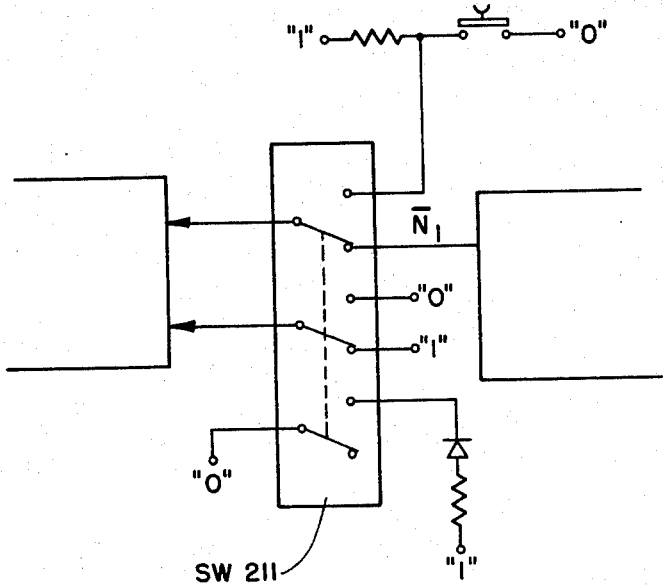
FIG. 22 shows the connection diagram of the READ-WRITE switch and the WRITE pulser.

The reading or writing commands carried out by these enabling signals are provided externally by the operator by means of the switch READ-WRITE and a pulser WRITE connected as in FIG. 22.

If the switch SW 211 (READ-WRITE) is in the READ position, the signal WREN remains stable at the value "1", whilst the signal $N_1$ provided for this specific purpose by the block A is supplied to the memory enable line MEN.

However when it is desired to carry out a data writing operation, the switch SW211 must be moved by the operator to the WRITE position. A luminous diode located on the control panel indicates that the switch is in this position.

The WREN enable remains in this case stable at the logic level "0" whilst the MEN signal is moved from the state "1" to "0" by the WRITE pulser. The memories only acquire the data supplied by the selector block when the pulser is depressed. Obviously the pulser is not operational in the case in which the switch is in the READ position, as this operation is automatically regulated by the alternation of the states "1" and "0" of the signal $\overline{N}_1$.

Display of the data which have been preset in the memories is regulated by the address of the reference scanning counter.

The frequency with which the reference of each channel are scanned depends on the frequency of the signal denoted by $CO\overline{N}_1CK$ 32, which steps up the counter. For this purpose use was made of the signal MEN taken from the read-write switch suitably divided into intervals of 32 oscillations by the component DUAL-4 bit-Binary Counter F4520 (FAIRCHILD) similar to that used for the same purpose in the sequential network of block A (FIG. 20).

The frequency of $CO\overline{N}_1CK$ 32 obtained in this way is 0.52 Hz. The limits referring to each channel therefore remains on the display for 1.92 sec. which enables the operator to receive the required visual information.

It should be noted that during the automatic operation of the apparatus, the scanning speed of the reference values (0.52 Hz) is equal to one thirty-second of the speed of the alternation of the parameter signals at the input of the converter.

Introduction to Blocks C and D—Operating modes

It has already been noted that the design of the apparatus was finalized in order to fulfil the requirements which may arise during extracorporeal circulation operations. The flexibility of the apparatus in effect enables operation with two different counting modes, scanning of the eight channels to be discontinued at any moment, or the programming of completed scanning discontinuation.

The elements which may be used by the operator to select the desired operating modes comprise the following external controls:
1. Selector of type of counting (AUTO-MANUAL switch 21—FIG. 2)
2. Selector of continuity or non-continuity of scanning (SINGLE SWEEP—CONTINUE switch 22—FIG. 2)
3. Pulser for enabling counting (START 23—FIG. 2)
4. Pulser for discontinuing counting (STOP 24—FIG. 2)
5. Manual step-up pulser (STEP-BY-STEP 25—FIG. 2).

Various combinations of the conditions of the switches provide four operating modes of different types, which may or may not require the associated use of the pulsers.

Figure 25:
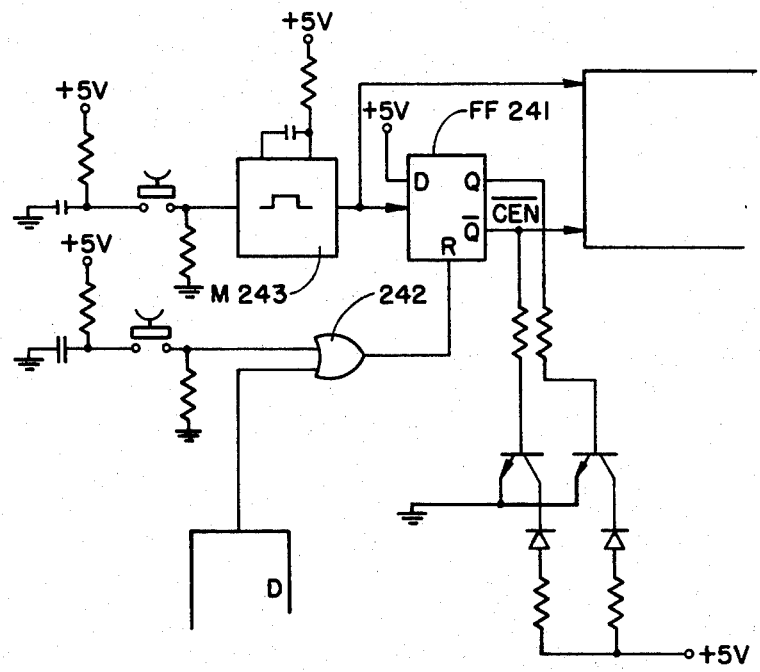
FIG. 25 is an internal diagram of block E.

FIG. 25 shows diagrammatically the conditons which cause the apparatus to function in the various modes.

Block C—Counting modes

Figure 2:
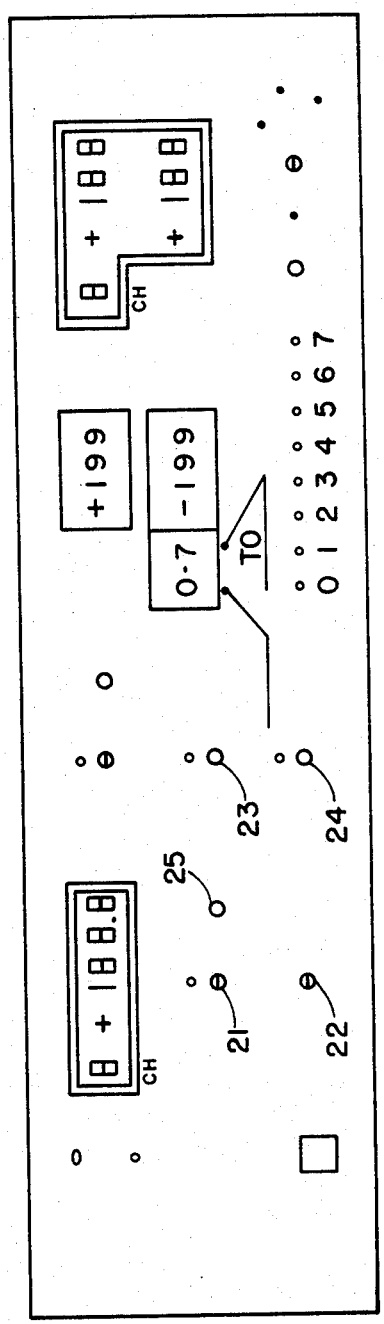
FIG. 2 is a diagram of the control panel of the apparatus of the invention.

The first decision-making level is the selection of the counting mode, and therefore the positioning of the AUTO-MANUAL switch 21 of FIG. 2.

Figure 23:
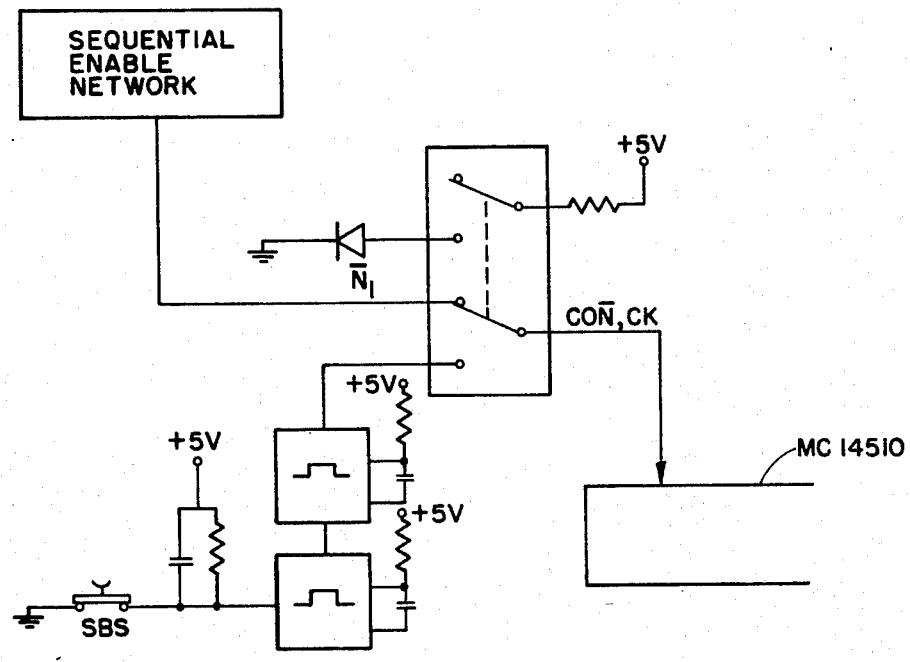
FIG. 23 is an internal diagram of block C shown in FIG. 1.

When the selector is in the AUTO position (see FIG. 23), the signal $\overline{N}_1$, previously generated by the sequential network of block A, is supplied to the counter block. This signal is denoted by $CO\overline{N}_1CK$ in order to indicate that it is used as the clock signal by the counter which regulates the scanning of the channels and because when it is active it coincides with $\overline{N}_1$. Each positive transition from "0" to "1" of the signal $\overline{N}_1 = CO\overline{N}_1CK$ steps up the address of the counter which therefore then functions at the same frequency with which the analogue-digital conversions are taking place.

However, if the switch is in the MANUAL position, this being indicated by the illumination of a luminous diode, the dependency of the counter on the converter A/D is discontinued. In this case the signal $CO\overline{N}_1CK$ only presents step-up transitions when the STEP-BY-STEP (SBS) pulser is depressed. The operator may therefore pause at will in the monitoring of a single parameter signal and pass on to the subsequent channel by means of manual action.

The rebounds within the STEP-BY-STEP pulser due to mechanical factors could cause more transitions on the generated signal MAN to correspond to a single depression of the pulser. In order to obviate this drawback, which would step-up the counter more than once, two monostables F4028 are connected in cascade and convert the signal MAN into a rectangular pulse MANU having a duration such as to cover the interval in which the mechanical oscillations take place.

Block D—Scanning modes

The second decision-making level for the selection of the operating mode of the apparatus is the positioning of the switch CONTINUE-SINGLE SWEEP. This switch enables programming of the inhibition of the counter when its address has reached the last of the scanning channels. For this purpose, the switch when in the SINGLE-SWEEP position, uses an end of scanning signal C>U supplied by the counter block and supplies it to the block E where the count inhibiting signal $\overline{CEN}$ (Count Enable) is generated.

In the CONTINUE position however, a signal fixed at the logic level "0" is supplied by the selector to the block E.

Figure 24:
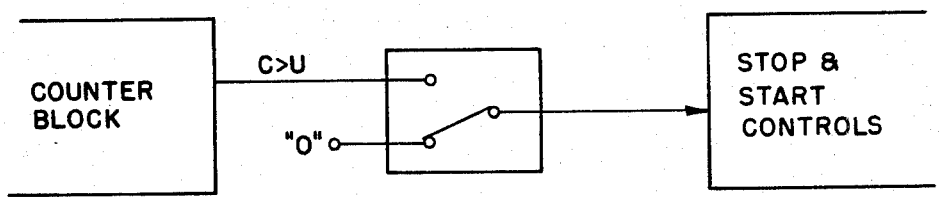
FIG. 24 is an internal diagram of block D.

FIG. 24 shows the connections of the switch.

Block E—STOP and START controls

The two pulsers STOP and START are connected to the remainder of the circuit as shown in FIG. 25.

Their controls are designed to inhibit or enable the counters, and are therefore mutually exclusive.

The condition of the outputs of the D-flip-flop FF 241 used to store the data from the pulsers is displayed by means of two luminous diodes, START being shown in green (output Q of the flip-flop) and STOP being shown in red (output $\overline{Q}$). The STOP pulses, generated by the depression of the relative pulser, are supplied to an OR-gate 242 with these pulses supplied from the block D. By re-setting the flip-flop FF 241, both these signals therefore bring the output $\overline{Q} = \overline{CEN}$ to the logic level "1" which in this case inhibits the operation of the counters.

The signal $\overline{COUNT\ ENABLE\ (CEN)}$ is at the level "0" and only enables counting after the flip-flop FF 241 has received a clock pulse generated by the depression of the START pulser, and remains at this level until a further reset is programmed.

The STOP output of the monostable M 243 disposed in series with the START pulser is used in the counter block.

It is useful to note that these two pulsers, in a different manner to the STEP-BY-STEP (SBS) pulsers, are operational during this type of operation of the apparatus.

Now that the decision-making elements which may be actuated by the operator have been described, it is necessary to show the combinations which may be obtained and the counting and scanning modes which may be obtained from this. As shown in FIG. 25, Four different situations may arise:

1. Automatic continuous scanning
   Position of the switches: AUTO and CONTINUE.
   The STEP-BY-STEP pulser is not operational.
2. Automatic single scanning
   Position of the switches: AUTO and SINGLE SWEEP.
   The STEP-BY-STEP pulser is not operational.
   At the end of scanning of the channels, the counters return to the STOP condition, and it is necessary to act on the START pulser to carry out further automatic scanning.
3. Manual continuous scanning
   Position of the switches: MANUAL and CONTINUE.
   The step-up of the Channel counter is decided by the STEP-BY-STEP pulser.
4. Manual single scanning
   Position of the switches: MANUAL and SINGLE SWEEP
   The step-up of the Channel counter is decided by the STEP-BY-STEP pulser.
   At the end of channel scanning, the counters move to the STOP position and the START pulser must be pressed in order to carry out further manual scanning.

Block F—Comparison of the address of the counters

It has already been noted (Block B) that the Channel counter which regulates the passage of the reference values from the memories to the comparison block, and the Reference counter which in contrast authorises scanning of these values on the appropriate display, have different counting speeds. In particular, during automatic operation, $f_{channels}=32\ f_{references}$, i.e. the frequency of the step-up $\overline{CON_1CK}\ 32$ of the Reference counter is 1/32 of that of the Channel counter. The variation limits which are read off the appropriate display must be coherent with respect to the channel number, also displayed, to which reference is made. It is therefore necessary for the enabling signal of the drivers and the latches which drive the illuminaton of the said displays to be supplied when the addresses of its counters, $C_3\ C_2\ C_1\ C_0$ and $K_3\ K_2\ K_1\ K_0$, coincide, in addition to their natural coincidence during the enable time interval of the memories.

This object is achieved by carrying out a comparison between the current addresses of the two counters and by supplying the output K=C to an AND-gate together with the signal DEN (Block A) which has been inverted previously.

The realization of the expression $\overline{DEN}+(K=C)$ thus enables coding of the clock signal FLICK of the latches (F4013) which maintain the information relating to the sign and the most significant bit of the references (U4, SU, S4, SL) before supplying it to the display of the most significant UPPER and LOWER digits. This signal is called FLICK, and suitably inverted it enables the drivers relating to U3, U2, L3 and L2 under the name of DREN.

Figure 26:
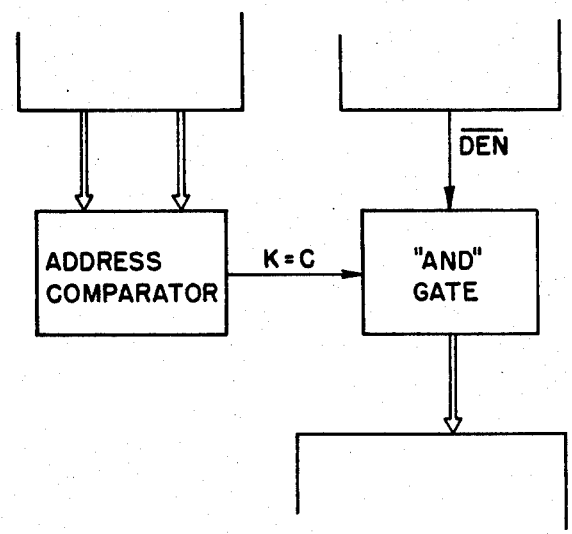
FIG. 26 is an operational diagram of block F.

The overall diagram of Block F is given in FIG. 26.

Channel scanning counter

The selection of monitoring several channels relating to the physical parameters of the perfusion circuit, which is one of the objects of the invention, provided certain complications relating to the structure of the timing block which regulates all the functions carried out by the circuit itself.

It is obvious that it would have been of little operational use, as well as extremely costly, in terms of time, space and cost, to provide eight separate blocks for the conversion and comparison of the individual signals with the respective references.

Use was therefore made of initial multiplexing of the channels which, as is known, requires as input the indication of the channel number to be selected at each instant. A second problem arose from the requirement of synchronizing the supply of the codes corresponding to the converted measurement to the comparison block and the codes of the values of the fixed limits (different for each parameter supplied by the memories.

The same timing signal successively enables the demultiplexer to close a switch on the channel line corresponding to that of the compared parameter in order to indicate the result of the monitoring.

Figure 27:
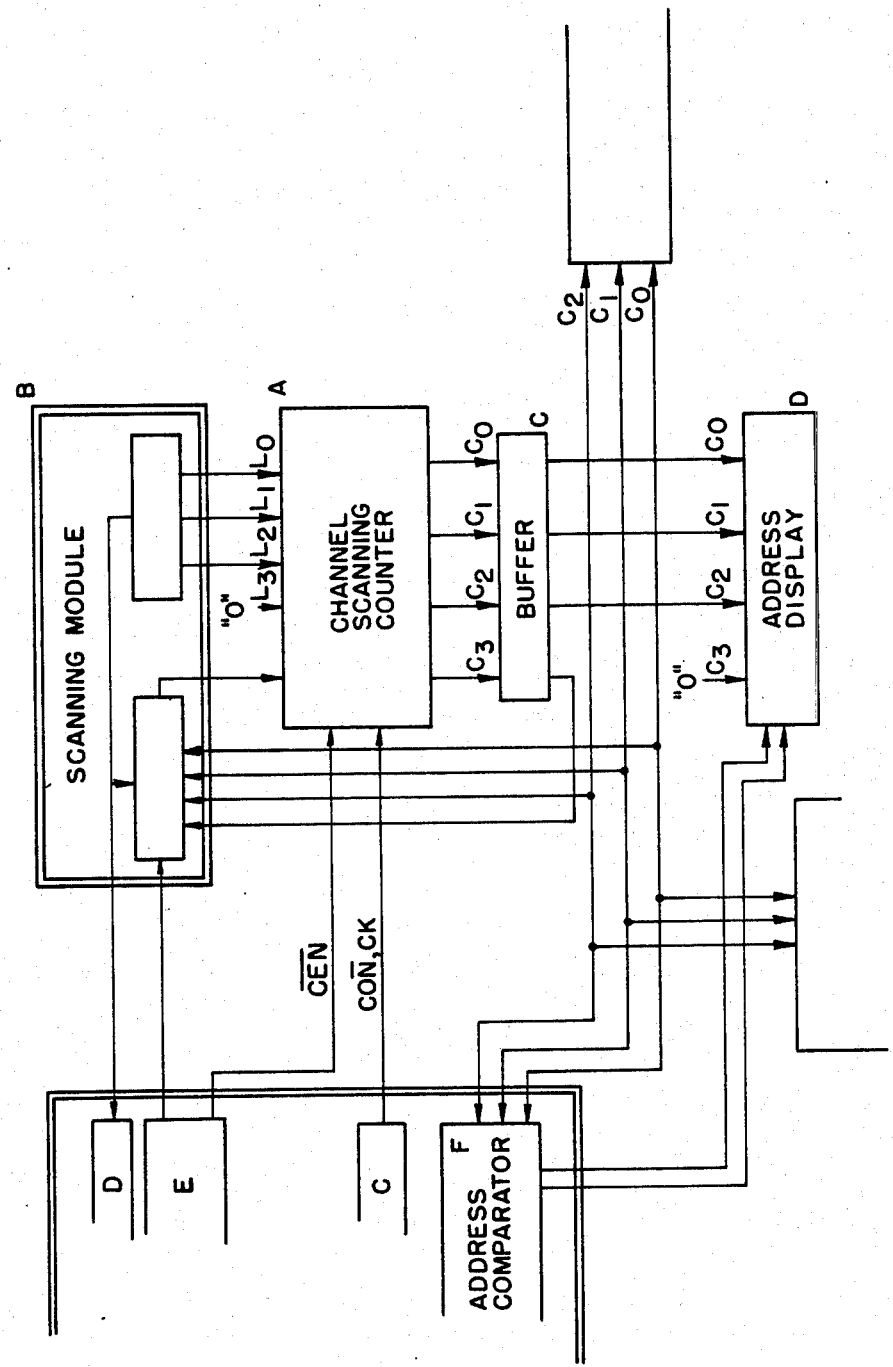
FIG. 27 is an operational diagram of the channel scanning block.
Figure 28:
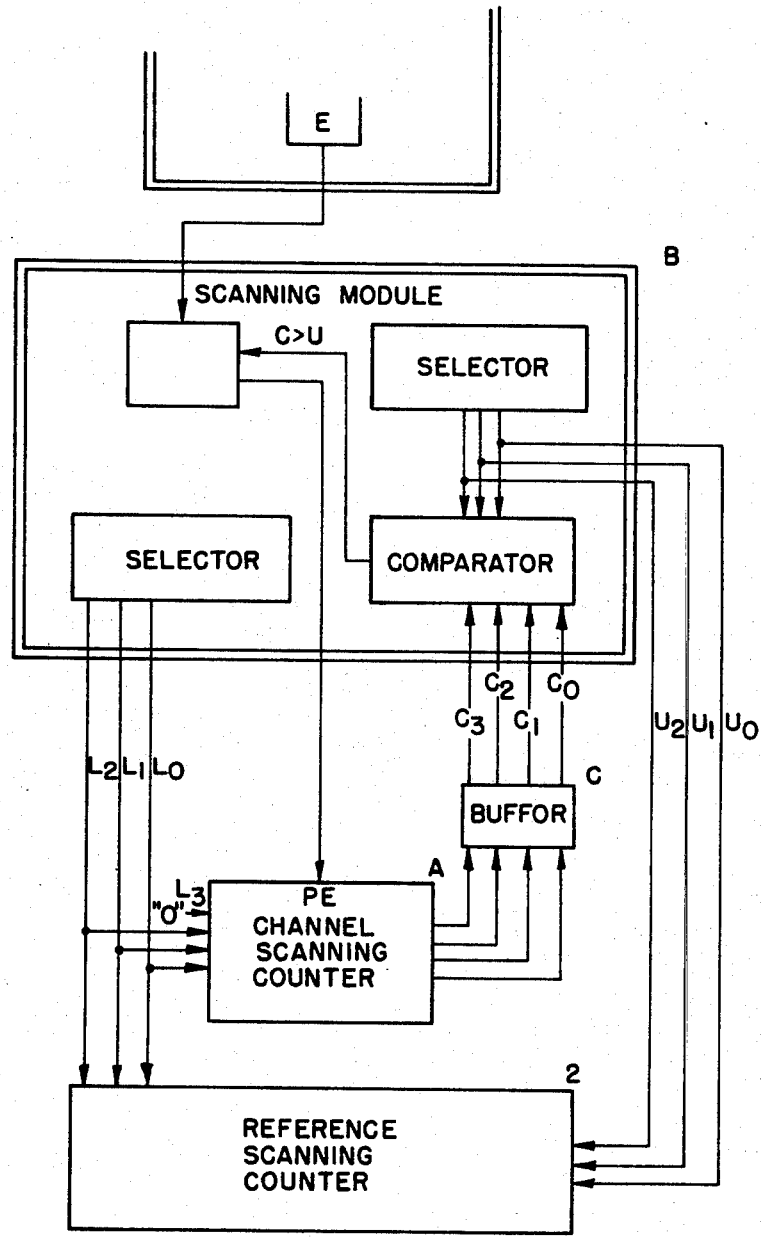
FIG. 28 is an internal diagram of the beginning and end of scanning block B.

The address which causes this synchronization is supplied by an UP/DOWN Decade Counter F4510 known as Channel Scanning Counter. An operational diagram of the block to which the counter belongs is shown in FIG. 27.

Block A—Channel Scanning Counter

The F4510 is an edge-triggered, synchronous, programmable counter with BCD output, constituted by a sequential network.

This counter was preferred as a result of the fact that it contains a programmable component, i.e. it may undertake other operations in addition to counting, such as the loading of a code at the input ($P_3\ P_2\ P_1\ P_0$) on the output ($Q_3\ Q_2\ Q_1\ Q_0$) on the basis of an asynchronous command active at the high level (PL), the zero-setting of the output corresponding to the high level of the Master Reset signal (MR).

When the enable signal $\overline{CE}$ (Count Enable) is at "0" and simultaneously at PL, the counter steps up its output by one at a positive transition of the clock CP.

In respect of the invention, the counter is required:

1. to count, in accordance with the counting modes (controlled step by step increase—MANUAL, STEP-BY-STEP—or automatic step-up—AUTO),
2. to cease counting at any moment required by the operator by means of the STOP control, independently of the step-up commands,
3. to provide the possiblity of externally controlling the beginning and end of scanning, in accordance with the particular requirements of an operation.

These requirements were achieved by acting in a suitable manner on the inputs of the F4510.

With respect to Para. 1, counting is regulated by the clock signal $\overline{CON_1CK}$ supplied by the AUTO-MANUAL switch. If this switch is in the MANUAL position, a pulse is supplied to the clock line each time that the STEP-BY-STEP pulser is depressed. However, if the switch is in the AUTO position, $\overline{N_1}$ is closed on $\overline{CON_1CK}$, $\overline{N_1}$ being supplied by the sequential ENABLE network, which transmits pulses of frequency $f_{\overline{N_1}}=f_{CO\overline{N_1}CK}=16.67$ Hz. The output $C_3\ C_2\ C_1\ C_0$ is stepped up at each positive transition of $\overline{CON_1CK}$.

In the case of complete eight channel scanning, each parameter signal is converted and compared with its limits every 0.52 seconds, which sampling is more than sufficient given the fact that the parameters being monitored are quasi static.

With respect to Para. 2, the command $\overline{CEN}$ output by the control logic block E causes the counter to cease by acting on the Count Enable input.

Block B—Beginning and end of scanning

As mentioned in Para. 3, it is possible to select monitoring of certain of the eight channels.

The flexibility of the apparatus in respect of the number of channels which it is desired to scan is obtained by means of the construction of block B of FIG. 27.

For the selection of the lower scanning limit, LOWER CHANNEL (FROM), a selector from the firm CONTRAVES operating with positive logic was used. This provides as output the code $L_2L_1L_0$ which constitutes the parallel load $P_2P_1P_0$ of the Channel counter. The output $L_3$ is hot connected, and the fourth charge bit $P_3$ is fixed at the level "0", as it is not provided for the counting to exceed seven (in binary code 0111). However, for selecton of the upper scanning limit, UPPER CHANNEL (TO), a further Contraves provides the required code $U_2U_1U_0$ on a comparator F40085, for technical details of which reference should be made to the comparison block.

The number of the channel of end of scanning is compared with the current scanning address, $C_3C_2C_1C_0$ supplied by the buffer (block C, FIG. 27).

The output signal C>U of the comparator indicates, when at level "1", that scanning has exceeded the preset upper limit; C>U therefore assumes the end of scanning significance.

This signal, after transfer to an OR-gate causes raising to level "1" of the output Q of a monostable F4528, known as LOADING, which constitutes the load input PE of the counter; this raise has a duration of 13 $\mu$sec (minimum interval required for a pulse of PL $t_wPL=60$ nsec) and is therefore sufficient to load on the outputs $Q_3Q_2Q_1Q_0 \equiv C_3C_2C_1C_0$ the beginning of scanning channel code $P_3P_2P_1P_0 \equiv L_3L_2L_1L_0$. With respect to the OR-gate located at the input of the LOADING monstable, this receives as input, in addition to the said END OF SCANNING signal, the possible STOP pulse supplied by the START and STOP control block, which causes, each time, the loading of the beginning of scanning code, irrespective of the state of the end of scanning signal.

Figure 32:
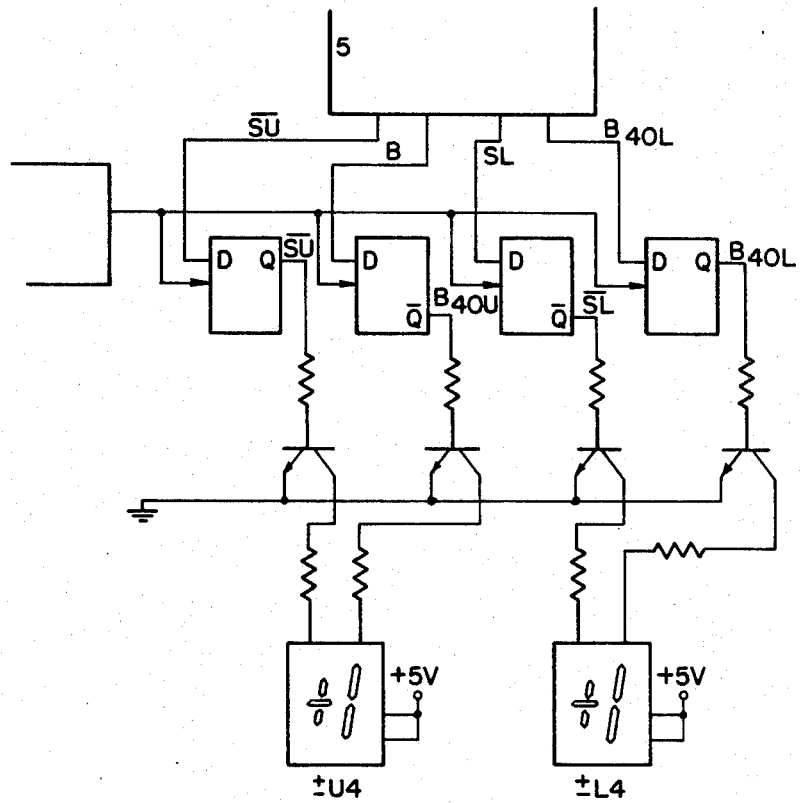
FIG. 32 shows the control configuration of the display units relating to the sign and the bit belonging to the fourth digit of the UPPER and LOWER references.

A diagram of the connections of block C for beginning and end of scanning is given in FIG. 32.

Block C—Buffer

The lines $C_3C_2C_1C_0$ are supplied to the buffers F4950, in order to increase the fan-out of the counter, as they constitute the inputs of a high number of integrated components.
1. The multiplexer and the demultiplexer
2. The memories
3. The comparator for the comparison of the addresses of the two counters (see block F)
4. The comparator belonging to the beginning and end of scanning block
5. The display associated with the channel corresponding to each converted measurement (see FIG. 27, block D).

Block D—Display of the current address

The address of the scanned channel is displayed continuously on a LITRONIX LD-702 display, driven by a driver F4511. Reference should be made to FIG. 12 for the connections required for this operation. In this application only three lines $C_2C_1C_0$ are supplied to the inputs of the driver, which lines enable the numbers of the channels from 0 to 7 to be displayed. The enable signal is always active (level "0").

Reference scanning counter

It has already been shown that it is necessary for the user to have available continuously, during an operation, the preset values of the upper and lower limits of each channel. The use of the alternative in which the references relating to each channel are preset on sixty-four contraves made it necessary to find another solution which satisfies this requirement.

The problem was resolved by using a second counter to scan on a display the UPPER (MAX) and LOWER (MIN) values at a frequency enabling the human eye to perceive the visual information.

It was decided to use for this purpose a clock ($CO\overline{N}_1CK$ 32) obtained from the signal MEN, whose frequency was suitably divided by 32, in order to control the step-up of the new reference counter. In this way:

$$f_{CO\overline{N}_1CK} = \frac{f_{CO\overline{N}_1CK}}{32}.$$

The component selected was identical to that constituting the channel scanning counter, i.e. an F4510 the parallel loading inputs of the code corresponding to the beginning of scanning channel were connected to the beginning of scanning selector ($L_2L_1L_0$) (see block C in the preceding paragraph). The command for loading on the outputs ($Q_3Q_2Q_1Q_0=K_3K_2K_1K_0$) of the code at the input is supplied by the level "1" of the output K>U of a comparator F40085 which compares the current address of the Reference counter with the code corresponding to the number of the end of scanning channel (see FIG. 30, block C).

The count enable control is the same as that of the channel counter control, i.e. the signal $\overline{CEN}$ supplied by the block E of the control logic. The output $K_2K_1K_0$, in addition to being displayed on a suitable display adjacent to the displays relating to the references, is again compared using a comparator F40085, but in this case with the current address of the Channel counter. This is dealt with further in the paragraph relating to the control logic, as it constitutes the block F.

Figure 29:
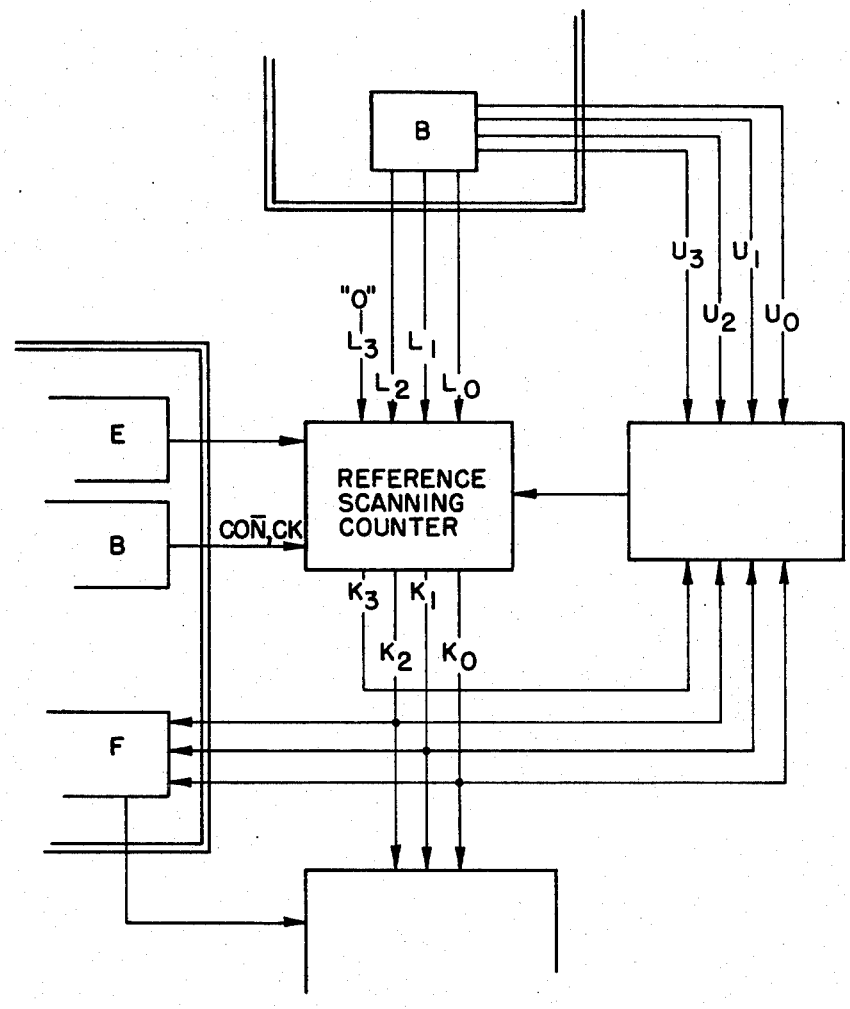
FIG. 29 is an operational diagram of the block to which the reference counter belongs.

An operating diagram of the block to which the Reference counter belongs is shown in FIG. 29.

Presetting of the variation limits and their storage

The limits of the parameter ranges which determine the physiological functioning of the perfusion circuit must be decided by the operator on the basis of the specific requirements of the operation in question, the required accuracy, and the various phases alternating during an operation of this type.

Considering the number of channels available on the alarm device, the presetting of the selected values causes the occurrence of a considerable number of variants. The separate programming of the references of each channel would have required the use of sixty-four selectors, in order to provide in parallel the information (160 bits) required for the comparison operation. A configuration of this type would have caused problems in the use of the device which would have compromised its efficiency, in addition to problems of cost.

These drawbacks were obviated by deciding to preserve the data with RAM memories and to preset them in sequence using only eight contraves. The latter are associated, for each writing operation, to the channel pre-selected by the operator. (see FIG. 30).

Figure 30:
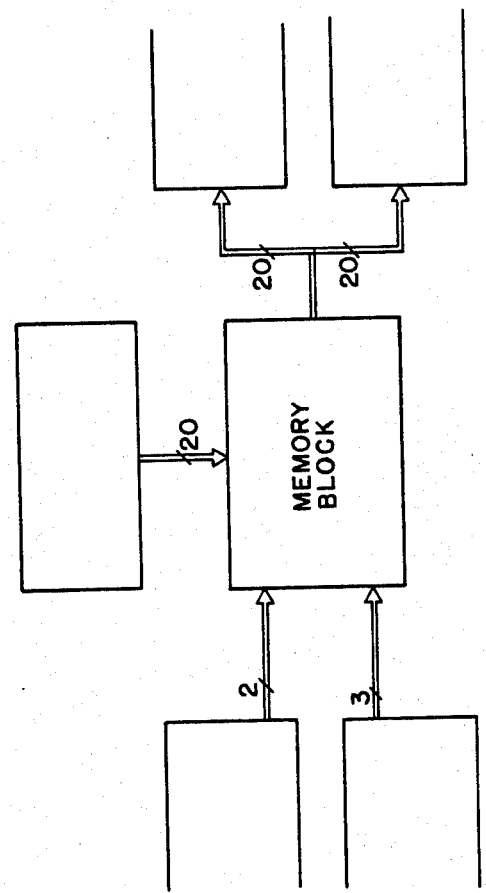
FIG. 30 is an operational diagram of the presetting and storage block for the variation limits.

A diagram of the block for presetting and storage of the data is given in FIG. 30.

In order to transfer the values preset by the eight selectors to the memories, the device must be in one of the two types manual continuous scanning modes or manual individual scanning.

The first decision to be made is therefore whether to use a manual counting mode (AUTO-MANUAL switch in the MANUAL position).

The selection of the type of scanning, individual or continuous, normally depends on the number of channels on which it is desired to preset data; the actuation of the START pulser when the end of one scanning operation is reached provides however the same mode of operation.

After having reached the required channel by means of the STEP-BY-STEP pulser, which may be monitored on the relative display, it is necessary to displace the reading and writing switch, which, during normal operation, should always be in the READ position, opposite to the WRITE position. It is only possible to enable transfer of the data from the selectors to the memories by depressing the WRITE pulser.

After repeating the writing operation for the required number of times, the operator should move the switch back to the READ position. In order to remind the operator to carry out this control, a luminous diode located above the writing controls remains illuminated during the entire data presetting operation.

The eight commutators of the CONTRAVES each code a decimal number in binary code by means of a selection disk. The printed circuit disposed on the disk (code) stripes fixed contact spring which transmit the corresponding bit configuration to the external connector.

The binary data is supplied to five memories MM74C89 64-bit TRI-STATE Random Access Read-Write Memory (NATIONAL) of the static CMOS type.

Figure 31:
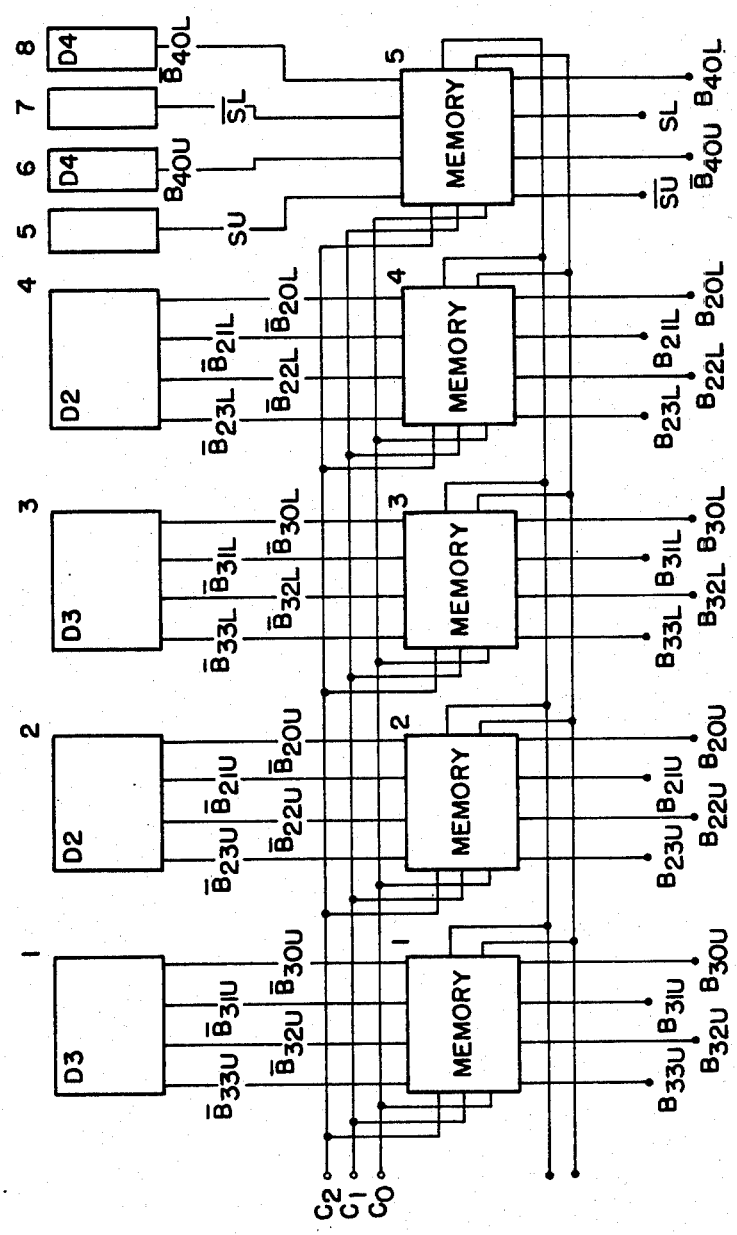
FIG. 31 is a diagram of the connections between the selectors and the memory.

The five memories which were used are connected to the selectors a shown in FIG. 31.

Display of the variation limits

The use of a block of memories to acquire and maintain the data preset externally by the operator has as its only drawback with respect to the operation of the device that it does not enable immediate visual monitoring of the previously selected values. It has already been mentioned that a possible alternative is to use sixty-four selectors in parallel as the interface between the user and the alarm system. This solution would have enabled simultaneous visual control of the data relating to the eight channels. The selection made to replace a configuration of this type resolves the requirement of visual feedback by displaying, a continuous cyclical sequence, the acquired data.

The values of the reference limits are therefore presented in sequence to the operator, together with the information from the channel in which the relative physical parameter is being processed.

In the case in which the device is programmed to carry out continuous monitoring of a single signal, scanning of all the channels of the reference limits is discontinued, and the references of the single channel in question are displayed permanently.

All these operations are carried out by the display block, by means of timing and enabling signals processed by the control logic block.

The frequency at which the data are scanned is determined by the Reference counter, and is 0.51 Hz.

Each pair of values UPPER (MAX) and LOWER (MIN) remains on the display for 1.96 secs which enables suitable reading.

The problem of timing this block was resolved, as explained above, by using the Reference counter and comparing its address $K_3$, $K_2$, $K_1$, $K_0$ with the address $C_3$, $C_2$, $C_1$, $C_0$ of the Channel counter.

Reading of the data written in the memories in fact takes place at the actual frequency of the latter, whilst it is preferable for the operator to display them at a slower rate of alternation. The signal DREN, suitably generated in the control logic block, enables the passage of the data supplied by the memories to the drivers which drive the displays corresponding to B2U, B3U, B2L and B3L, in addition to the channel display.

The drivers F4051 maintain on internal latches the data at the address inputs in correspondence to the state "0" of the enabling signals DREN. Reference should be made to FIG. 12 for the connection between this integrated component and the common cathode display LITRONIX DL-702.

The channel number displayed corresponds to the address $K_2$, $K_1$ and $K_0$ of the Reference counter.

In order to drive the displays relating to the sign and bit belonging to the fourth digit of the references UPPER (MAX) and LOWER (MIN) (SU, $B_{40U}$, SL, $B_{40L}$), use was made of transistors polarised by the outputs of four D-flip-flops F4013 (FIG. 32).

The bistables (edge triggered) receive the clock pulses from the signal FLICK, processed in the control logic block, and store the data at the input D at the moment of the FLICK transition.

In order to obtain the data required for a correct display, the outputs Q of the flip-flops corresponding to $B_{40U}$ and SL are taken, in such a way as to supply to the display a level "0" for positive polarities of the references UPPER (MAX) and LOWER (MIN) ($\overline{SU}$ and $\overline{SL}$) and the correct positive logic code for the fourth digits B4U and B4L ($B_{40U}$ and $B_{40L}$).

Two common anode LITRONIX DL-701 displays are used to show these four signals.

A list of the discrete components, and corresponding values, used in the diagram of FIGS. 33A–33D is now given by way of non-limiting example.

| Values in Kohm | Resistors |
|---|---|
| 0.1 | $R_{44}$, $R_{46}$, $R_{49}$ |
| 0.16 | $R_A$, $R_B$, $R_C$, $R_D$, $R_E$, $R_J$ |
|  | $R_{43}$, $R_{45}$, $R_{47}$, $R_{61}$ |
| 0.22 | $R_9$, $R_{11}$, $R_{18}$, $R_{34}$, $R_{35}$, $R_{36}$ |
|  | $R_{37}$, $R_{38}$, $R_{39}$, $R_{40}$, $R_{41}$, $R_{64}$, $R_{66}$ |
| 0.3 | $R_{67}$ |
| 0.82 | $R_{70}$ |
| 1 | $R_4$ |
| 1.5 | $R_2$ |
| 2.2 | $R_{21}$, $R_{23}$ |
| 2.7 | $R_{53}$, $R_{55}$, $R_{71}$ |
| 3.3 | $R_{20}$, $R_{22}$, $R_{24}$, $R_{42}$ |
| 4.7 | $R_1$, $R_8$, $R_{10}$, $R_{17}$, $R_{63}$, $R_{65}$ |
| 8.5 | $R_3$, $R_{52}$, $R_{54}$, $R_{56}$, $R_{62}$ |
| 10 | $R_0$ |
| 15 | $R_F$, $R_G$, $R_H$, $R_L$, $R_M$, $R_N$, $R_O$, $R_{13}$, $R_4$ |

-continued

| | |
|---|---|
| 18 | $R_{15}, R_{26}, R_{27}, R_{28}, R_{29}, R_{30}$ |
| | $R_{31}, R_{32}, R_{33}$ |
| 33 | $R_6$ |
| 47 | $R_{12}$ |
| 100 | $R_5, R_{48}, R_{49}, R_{50}, R_{58}, R_{59}, R_{60}$ |
| 150 | $R_7$ |
| 680 | $R_{57}$ |
| 1000 | $R_{51}$ |
| Kohm | Trimmers |
| 0.1 | $T_3$ |
| 2 | $T_1$ |
| 100 | $T_2$ |
| pF, nF, μF | Capacitors |
| 22 pF | $C_3, C_8$ |
| 68 pF | $C_{13}, C_{14}, C_{15}$ |
| 200 pF | $C_1$ |
| 500 pF | $C_5, C_6, C_7$ |
| 8.2 nF | $C_2$ |
| 22 nF | $C_{16}$ |
| 0.1 μF | $C_{18}$ |
| 0.947 μF | $C_{12}$ |
| 6.4 μF | $C_9, C_{10}, C_{11}$ |
| 22 μF | $C_{17}$ |
| 220 μF | $C_4, C_{20}$ |

| ABBREVIATION AND FUNCTION | CORRESPONDENCE IN THE DIAGRAM OF FIGS 39A–39D |
|---|---|
| μA 760 Differential Comparator | 1.1 |
| LD 110 ⎫ A/D Converter | 1.2 |
| LD 111 ⎭ | 1.3 |
| LF 311 Voltage Comparator | 1.4 |
| MC 14050 Buffer | 3.7 |
| MC 14002 Nor Gate | 1.6 |
| MC 14013 CD Flip-flop | 1, 7, 1.11, 2.15, 2.16, 3.7, 4.22 4.23, 4.24, 4.25 |
| MC 14520 Up Counter | 1.8, 3.11 |
| MC 14011 Nand GAte | 1.9 |
| MC 14027 JK Flip-flop | 1.10 |
| F 4528 Monostable | 1.12, 1.13, 3.1, 3.2 |
| F9LS175 Quad D-Flip-flop | 1.14, 1.15 |
| MM 74089 RAM | 2.1, 2.2, 2.3, 2.4, 2.5 |
| F 40085 Magnitude Comparator | 2.6, 2.7, 2.8. 2.9. 3.8, 3.9, 3.10 |

| ABBREVIATION AND FUNCTION | CORRESPONDENCE IN THE DIAGRAM OF FIGS 33A–33D |
|---|---|
| MC 14081 And Gate | 2.10, 2.12, 3.12 |
| MC 14071 Or Gate | 2.11, 2.13, 3.4 |
| MC 14049 Inverter | 2.14, 1.5 |
| F 4051 Demultiplexer | 2.17, 3.13 |
| MC 14010 Up-Down Counter | 3.5, 3.6 |
| F 4511 Driver | 4.1, 4.2, 4.3, 4.4, 4.5, 4.6, 4.7 4.8, 4.9 |
| LD-702 Display Litronix | 4.10, 4.12, 4.13, 4.14, 4.15, 4.17, 4.18, 4.20, 4.21 |
| LD-701 Display Litronix | 4.11, 4.16, 4.19 |
| CA 3081 Transistor Array NPN | 4.26, 4.27, 1.16 |

A specific example of use of the proposed apparatus is now given, with reference to FIG. 2 which shows a diagram of the control panel of the apparatus.

By depressing the pulser "STORE" the limit values of the fields of variation are preset in static RAM memories; this operation is carried out while the READ-WRITE switch is in the WRITE position. It is interesting to note that it is possible to vary these values during the operation of the apparatus. This enables, for example, a restriction of the range of the values and thus more accurate monitoring of signals which, depending on the circumstances, seem particularly critical or important. There are provided two selectors to select the channel number in which scanning is to take place, in order to enable a partial use of the apparatus.

The operations which refer to each channel are carried out in a cyclical sequence.

The AUTO-MANUAL switch enables control of scanning, and when in the AUTO position enables control by an internal timer which allows 60 msec. to each signal, and when in the MANUAL position enables control by the external action of an operator. By depressing the STEP-BY-STEP pulser the channel number in question is stepped up.

The switch CONTINUE-SINGLE SCAN enables either continuous scanning of the selected channels (CONTINUE), which may only be discontinued by the STOP pulser, or single scanning (SINGLE SCAN) controlled by the START pulser.

The combined use of the various switches and pulsers enables a considerable degree of flexibility in operation, with four different modes of operation:

1. Automatic and continuous scanning: switches in AUTO and CONTINUE SCAN positions. The STEP-BY-STEP pulser is not operative.

2. Automatic single scanning: switches in AUTO and SINGLE SCAN positions. The STEP-BY-STEP pulser is not operative. At the end of scanning the apparatus moves into the STOP position. In order to obtain further scanning, press the START pulser.

3. Continuous manual scanning: switches in MANUAL and CONTINUE positions. The channel number in question may be stepped up by pressing the STEP-BY-STEP pulser.

4. Manual single scanning: switches in MANUAL and SINGLE SCAN positions. The channel number in question may be stepped up by pressing the STEP-BY-STEP pulser. At the end of scanning of a group of channels the apparatus moves into the STOP position. In order to obtain further scanning press the START pulser.

In addition to the qualitative alarm operation, the apparatus provides quantitative data by means of a display which shows the instantaneous value of the individual variables together with the corresponding channel number.

The apparatus is designed using digital and integrated circuit techniques of the CMOS type.

The block diagram of FIG. 1 shows in a simplified manner the flow of data between the various blocks and the internal structure of the apparatus.

The signals supplied by the transducers are scanned at a frequency determined by the CHANNEL SCANNING COUNTER and are then supplied to the CONVERSION block. The output of the A/D converter is coded in BCD and consists of 3½ digits.

A display shows the result of the conversion. The binary data of the most significant 2½ digits is supplied to the COMPARISON block. In this block the value of the parameter is compared with the upper and lower limits contained in the RAM memory cells. This operation supplies a signal ERROR associated with the channel under examination. If the signal is at the logic level TRUE the apparatus actuates the acoustic and luminous alarm.

The CHANNEL SCANNING COUNTER supplies the correct address to the multiplexer, the display and the memory block, ensuring that the converted signal and the band limits correspond. The same address is then supplied to the final demultiplexer which then sends the signal ERROR to the corresponding luminous warning lamp.

An END OF CONVERSION signal EOC, supplied by the conversion block 2, is processed by means of the CLOCK signal within the CONTROL LOGIC block. In this block, a sequential network 8 generates important enabling signals used by the demultiplexer 5, the memories and the two counters. The second counter designated by REFERENCE LIMIT SCANNING COUNTER controls the frequency at which the values of the limits of the variation bands and the corresponding channel number appear on an appropriate display. This frequency corresponds to one thirty-second of the frequency of the first counter, thereby enabling the values to remain on display for a suitable period of time. The A/D conversion is carried out by two monolithic processors; each conversion is the result of a fixed number of successive approximations which improve the accuracy of the measurement using a "quantified load feedback" technique.

The device of the invention is designed to cover an aspect of operating theatre instruments which has up to now been left aside by manufacturers of biomedical apparatus.

An advantage of the device of the invention lies in the fact that it provides a simple solution of a flexible nature to the problem of the simultaneous control of several factors relating to extra corporeal perfusion.

The use of digital techniques enables considerable accuracy and optimum reproduction of the comparison between the sampled data and its variation range.

The flexibility of the system for pre-setting the band limits on the individual channels and the number of channels to be sampled is particularly advantageous and novel. The number of channels to be sampled may be varied at any moment by simply actuating the rotary numbered switches. The band limits of the individual channels may be varied at any moment by changing the comparison values contained in the RAMs by means of the STORE pulser.

The apparatus is therefore very useful for following the delicate transitional phases of beginning and end of extracorporeal perfusion.

The use of apparatus of this type therefore reduces to a minimum the required involvement in the operation of apparatus for extracorporeal perfusion and the medical and nursing staff may give their entire attention to medico-surgical problems without becoming involved in the monitoring of mechanical components.

Given the size of the general description of the apparatus of the invention, it was not considered necessary to describe in detail the operating principles of certain of the components shown in the drawings, as it was considered that the overal functioning of the apparatus would be obvious to persons skilled in the art on the basis of the preceding detailed description. In addition, it should be emphasised that various modifications and variants may be made to the invention, for the most part designed to substitute equivalent elements, on the condition that these do not depart from the spirit and the scope of the invention.

We claim:

1. A multichannel programmable band comparators for use in cardiac surgery, comprising a plurality of transducers adapted to provide signals indicative of physical parameters of a patient, a multiplexer connected to said transducers to multiplex the signals thereof; an analog-to-digital converter connected to said multiplexer to receive the multiplexed signals therefrom and to convert such signals into digital form; an oscillator which generates an external clock timing signal which is conveyed to said analog-to-digital converter; a memory block disposed to receive and store digital form information representing upper limit and lower limit values of said parameter; a comparator block arranged to compare signals from said analog-to-digital converter with said upper limit and lower limit values obtained from said memory, a first counter that supplies the address of a parameter channel under examination to both said multiplexer and said memory to ensure correspondence between said analog-to-digital converter signals and upper limit and lower limit signals; a control logic block connected to an output of said oscillator and to an output of said analog-to-digital converter, and alarm means connected to the output of said comparator block, said alarm means comprising a demultiplexer which receives said address from the first counter and from which alarm signals are supplied, and an alarm device connected to said demultiplexer to produce a visual and acoustic alarm when any of said signals from said analog-to-digital converter is outside said upper limit and lower limit values, and wherein said analog to digital converter supplies an end of conversion signal EOC, a control logic block connected to an output of said oscillator and to on output of said analog-to-digital converter in which said end of conversion signal EOC is processed together with a timing signal provided by said oscillator and which generates an enabling signal DEN for said demultiplexer to pass information on to said alarm device only when said end of conversion signal EOC has been received by said logic block.

2. An apparatus according to claim 1, wherein said memory block has adjusting means whereby said upper limit and lower limit values in said memory block are adjustable.

3. An apparatus according to claim 1, wherein said comparator block has means for comparing a variable number of body parameter signals.

4. An apparatus according to claim 1, further comprising an AUTO-MANUAL switch operable to selectively present said parameter signals for memory block comparison in a selected order; and an internal timer for automatic operation when said switch is in the auto position.

5. An apparatus according to claim 1, further comprising means to indicate the number of the individual body parameters being analyzed in said comparator block.

* * * * *